US008816068B2

(12) United States Patent
Kuusisto et al.

(10) Patent No.: US 8,816,068 B2
(45) Date of Patent: Aug. 26, 2014

(54) HYDROGENATION PROCESS FOR THE PRODUCTION OF A SUGAR ALCOHOL

(75) Inventors: Jyrki Kuusisto, Vantaa (FI); Heikki Heikkilä, Espoo (FI); Matti Tylli, Kantvik (FI); Martin Golde, Joensuu (FI); Teppo Riihimäki, Pori (FI)

(73) Assignees: Schott Solar AG, Alzenau (DE); Dupont Nutrition Biosciences Aps, Copenhagen K (DK)

( * ) Notice: Subject to any disclaimer, the term of this patent is extended or adjusted under 35 U.S.C. 154(b) by 1131 days.

(21) Appl. No.: 12/298,714

(22) PCT Filed: Apr. 26, 2007

(86) PCT No.: PCT/FI2007/050235
§ 371 (c)(1),
(2), (4) Date: Oct. 27, 2008

(87) PCT Pub. No.: WO2007/125176
PCT Pub. Date: Nov. 8, 2007

(65) Prior Publication Data
US 2009/0076260 A1 Mar. 19, 2009

(30) Foreign Application Priority Data
Apr. 27, 2006 (GB) .................................. 0608376.0

(51) Int. Cl.
C07H 1/00 (2006.01)
C07H 3/00 (2006.01)
C08B 37/00 (2006.01)
C07C 29/141 (2006.01)

(52) U.S. Cl.
CPC .................................. C07C 29/141 (2013.01)
USPC ....................................................... 536/124

(58) Field of Classification Search
CPC .................................................... C07C 29/141
USPC ....................................................... 536/124
See application file for complete search history.

(56) References Cited

U.S. PATENT DOCUMENTS

| 2,292,293 | A | 8/1942 | Rode et al. |
| 3,763,246 | A | 10/1973 | de Berardinis et al. |
| 3,963,788 | A | 6/1976 | Kruse et al. |
| 4,433,184 | A | 2/1984 | Huibers et al. |
| 4,510,339 | A | 4/1985 | Arena |
| 5,162,517 | A | 11/1992 | Darsow |
| 6,124,443 | A | 9/2000 | Darsow |
| 6,441,255 | B1 | 8/2002 | Haas et al. |
| 6,486,366 | B1 | 11/2002 | Ostgard et al. |
| 6,570,043 | B2 | 5/2003 | Elliott et al. |
| 2006/0009661 | A1 | 1/2006 | Arndt et al. |

FOREIGN PATENT DOCUMENTS

| EP | 0004721 | 10/1979 |
| GB | 354196 | 8/1931 |
| GB | 0625171 | 6/1949 |
| GB | 1129586 | 10/1968 |
| JP | 2001079411 | 3/2001 |

OTHER PUBLICATIONS

"Raney Nickel" from Chemical Book [online], [Retrieved on Mar. 3, 2011]. Retrieved from the internet <http://www.chemicalbook.com/ChemicalProductProperty_EN/CB4129561.htm>.*
Albert, R. et al., "Die Katalytische Herstellung von Zuckeralkoholen und deren Verwendung" Chem.-Ing.-Tech (1980) pp. 582-587, vol. 52(7).
Linko, P. et al., "Carbohydrate Sweeteners in Foods and Nutrition" Academic Press (1980) pp. 243-257.
Arena, BJ, "Deactivation of Ruthenium Catalysts in Continuous Glucose Hydrogenation" Applied Catalysis A: General (1992) pp. 219-229, vol. 87.
Hoffer, BW et al., "The Role of the Active Phase of Raney-type Ni catalysts in the Selective Hydrogenation of D-Glucose to D-Sorbitol" Applied Catalysis A: General (2003) pp. 437-452, vol. 253.
Besson, M. et al., "Deactivation of Metal Catalysts in Liquid Phase Organic Reactions" Catalysis Today (2003) pp. 547-559, vol. 81.
Hu, M. et al., "HPLC and NMR Study of the Reduction of Sweet Whey Permeate" Journal Agric. Food Chem. (1996) pp. 3757-3762, vol. 44.
Hendriks, Hej et al., "The Effect of Bismuth on the Selective Oxidation of Lactose on Supported Palladium Catalysts" Carbohydrate Research (1990) pp. 121-129, vol. 204.
De Wit, G. et al., "Catalytic Dehydrogenation of Reducing Sugars in Alkaline Solution" Carbohydrate Research (1981) pp. 125-138, vol. 91.
Fabre, L. et al., "Catalytic Hydrogenation of Arabinonic Acid and Arabinonolactones" Catalysis Communications (2001) p. 249-253, vol. 2(8), English Abstract only.
Mikkola, JP et al., "Deactivation Kinetics of Mo-Supported Raney Ni Catalyst in the Hydrogenation of Xylose to Xylitol" Applied Catalysis A: General (2000) pp. 143-155, vol. 196(1).
Park, K. et al., "Current Efficiencies and Regeneration of Poisoned Raney Nickel in the Electrohydrogenation of Glucose to Sorbitol" Journal of Applied Electrochemistry (1986) pp. 941-946, vol. 16.
Kuusisto, J. et al., "Hydrogenation of Lactose Over Sponge Nickel Catalysts-Kinetics and Modeling" Industrial & Engineering Chemistry Research (2006) pp. 5900-5910, vol. 17.

* cited by examiner

Primary Examiner — Scarlett Goon
(74) Attorney, Agent, or Firm — Scully, Scott, Murphy & Presser, P.C.

(57) ABSTRACT

The invention relates to an improved process for the production of a sugar alcohol from the corresponding sugar through catalytic hydrogenation. Especially, the invention relates to a process for reducing the interference of sugar-derived aldonic acids in the hydrogenation process by adjusting the hydrogenation conditions so that the activity of the catalyst is maintained. In one embodiment of the invention, the process of the invention is carried out by adjusting the hydrogenation temperature by starting the hydrogenation at a lower temperature and then gradually rising the temperature to the final hydrogenation temperature. In another embodiment of the invention, the process of the invention is carried out by adding small-molecular monocarboxylic acids to the hydrogenation solution.

37 Claims, 24 Drawing Sheets

HYDROGENATION PROCESS FOR THE PRODUCTION OF A SUGAR ALCOHOL

FIELD OF THE INVENTION

The present invention relates to an improved process of hydrogenating sugars to corresponding sugar alcohols. Especially, the invention relates to a process for reducing the interference of sugar-derived carboxylic acids, especially aldonic acids in the catalytic hydrogenation of a sugar to the corresponding sugar alcohol. The invention may be especially applied to the hydrogenation of aldose sugars to alditols, for example the hydrogenation of lactose to lactitol.

BACKGROUND OF THE INVENTION

The interest toward special sugars and sugar alcohols has recently increased due to the interesting functional properties of some special sugars and sugar alcohols, such as xylitol. Because of the non-cariogenic properties and the reduced calorie value of sugar alcohols compared to conventional carbohydrate sweeteners, sugar alcohols are suitable for the production of non-cariogenic and reduced-calorie (light) products and products with a defined nutritional purpose (e.g. products for diabetics). The sugars of interest may be monosaccharides, disaccharides or higher saccharides. The best-known special sugar alcohols (alditols) are xylitol and sorbitol, but even other sugar alcohols, such as lactitol, maltitol and mannitol have recently gained more interest and more market.

Sugar alcohols may be commercially produced from the corresponding sugars through catalytic hydrogenation. Alditol sugars, such as lactitol, mannitol, sorbitol, xylitol, maltitol etc. are thus produced by the catalytic hydrogenation of the corresponding aldoseses, i.e. lactose, mannose, glucose, xylose and maltose. Sponge type nickel catalysts, such as Raney nickel catalysts represent one example of the catalysts generally used in the hydrogenation of sugars, such as in the hydrogenation of aldoses and ketoses to corresponding alditols.

One of the problems encountered in the catalytic hydrogenation of aldose sugars is the deactivation and unstability of the hydrogenation catalyst, for example due to the formation of harmful by-products, such as epimers, hydrolysis products and their reduction products. Aldonic acids, such as lactobionic acid and xylonic acid, represent one example of the harmful by-products formed in the hydrogenation of aldoses to alditols. In the hydrogenation of glucose, it has been found that gluconic acid is typically formed as a by-product. It has also been found that gluconic acid has a tendency to adhere to the catalyst surface thus occupying the active sites of the hydrogenation catalyst and deactivating the catalyst. The deactivation and unstability of the catalyst also lead into problems in the recovery and regeneration of the catalyst. These problems are even more severe specially with recycled catalysts. Recovery of the catalyst by filtration may be difficult.

In the hydrogenation of lactose, for example too high temperatures may lead to the hydrolysis of lactose, whereby galactitol and sorbitol are formed as by-products. As a still further by-product, lactulose is formed due to the isomerisation of lactose, especially at a too high pH. Lactulose is further hydrogenated to lactulitol and lactitol.

R. Albert et al. describe the catalytic production of sugar alcohols and their use in Chem-Ing.-Tech 52 (1980), Nr. 7, p. 582-587. The article surveys numerous applications of the principal sugar alcohols sorbitol and xylitol. It is recited that the industrial production of sugar alcohols takes place almost exclusively by catalytic hydrogenation of the corresponding sugars. Sorbitol is thus manufactured by hydrogenation of D-glucose, xylitol by hydrogenation of xylose and mannitol and sorbitol by hydrogenation of invert sugar or fructose (over sponge nickel catalyst fructose is hydrogenated to both mannitol and sorbitol in approximately equal amounts). Raney nickel is recited to be an especially preferred catalyst. A temperature in the range of 120 to 150° C. is recited as a suitable hydrogenation temperature for the hydrogenation of glucose to sorbitol. The formation of D-gluconic acid as a by-product through the Cannizzaro reaction is also disclosed.

P. Linko et al. describe the preparation, characteristics and potential applications of lactitol in Carbohydrate Sweeteners in Foods and Nutrition, ed. by Pekka Koivistoinen and Lea Hyvönen, University of Helsinki, Academic Press 1980, p. 243-257. The reference discloses reduction with sodium borohydride and catalytic hydrogenation as potential methods for the production of lactitol. Temperatures in the ranges of 100 to 200° C. depending on the hydrogenation pressure are described for the hydrogenation of lactose to lactitol. It is also recited that severe reaction conditions, for example high temperatures (130° C.) lead into the formation of by-products, such as lactulose (by epimerization) and galactose and glucose (by hydrolysis), which in turn are partially hydrogenated to corresponding sugar alcohols lactulitol, galactitol and sorbitol. It is also recited that lactitol is partially decomposed under severe reaction conditions.

Blaise J. Arena (UOP) has studied the deactivation of ruthenium catalysts in continuous hydrogenation of glucose in Applied Catalysis A, General, 87 (1992), p. 219-229, Elsevier Science Publishers B.V., Amsterdam. In this study, several $Ru/Al_2O_3$ glucose hydrogenation catalysts were tested in continuous operation. After use, spent catalysts were examined to determine what changes had accompanied deactivation. One of these changes was found to be the build-up of gluconic acid on the catalyst and poisoning of the catalyst by gluconic acid during use.

B. W. Hoffer et. al discuss the role of the active phase of Raney-type Ni catalysts and their Ni—Al alloy precursors in the selective hydrogenation of D-glucose to D-sorbitol in Applied Catalysis A: General 253 (2003), p. 437-452. It is recited that Raney-type Ni catalysts lose Ni and Al at the applied reaction conditions. Furthermore, it is recited that the major cause of deactivation of Raney-type Ni catalysts is the presence of D-gluconic acid formed during the reaction, because D-gluconic acid blocks the Ni sites of the catalyst.

M. Besson et al. discuss the deactivation of metal catalysts in liquid phase organic reactions in Catalysis Today 81 (2003), p. 547-559. The hydrogenation of glucose to sorbitol on Ru/C catalysts has been studied. It is recited that the main by-products are gluconic acid formed by the Cannizzaro reaction and mannitol formed by sorbitol epimerization. Furthermore, it was generally concluded that the main causes of catalyst deactivation are metal and support leaching, deposition of inactive metal layers or polymeric species, and poisoning by strongly adsorbed species.

Ming Hu et al. have presented HPLC and NMR study of the reduction of sweet whey permeate in J. Agric. Food Chem. 1996, 44, p. 3757-3762. It is recited that with a reaction time of 4 hours, an initial hydrogen pressure of 1500 psi, Raney Ni catalyst, and a temperature of 120° C., sweet whey permeate gives lactitol (85.2%), lactulitol (1.7%) and sorbitol and dulcitol (0.8%).

H. E. J. Hendriks et al. have studied the effect of bismuth on the selective oxidation of lactose to sodium lactobionate on supported palladium catalysts at temperatures up to 333 K (60° C.) in Carbohydrate Research, 204 (1990), p. 121-129. It is recited that fifteen batches of lactose were oxidized with the same charge of catalyst without significant loss in initial activity or selectivity. It is also recited that other aldoses such as maltose, glucose and galactose could be oxidized analogously with similar activities.

G. de Wit has studied the catalytic dehydrogenation of reducing aldose sugars to aldonic acids in alkaline solution in Carbohydrate Research 91 (1981), p. 125-138. The dehydrogenation was carried out in alkaline medium under the catalytic action of platinum or rhodium.

U.S. Pat. No. 4,433,184, HRI Inc. (published Feb. 21, 1984) discloses a process for producing a high-purity alditol, such as sorbitol by catalytic conversion of the corresponding monosaccharide sugar to an alditol, whereby the pH of the reaction liquid in the hydrogenation zone is controlled to a value between 4.5 and 7 by adding an alkali solution, such as sodium hydroxide to the hydrogenation feed. The hydrogenation temperature was 130 to 180° C. and the hydrogenation pressure was 500 to 2000 psig. High-activity nickel on an inert support was used as the catalyst. It was found that the alkali addition substantially prevented the undesirable formation of acids such as gluconic acid in the hydrogenation zone, thus preventing the acid leaching of active metals from the catalyst and thereby maintaining high catalyst activity and a long catalyst lifetime.

U.S. Pat. No. 4,510,339, UOP Inc., Blaise J. Arena (published Apr. 9, 1985) discloses an improved method of hydrogenating carbohydrates to corresponding polyols using a group VIII metal as the hydrogenation catalyst, whereby hydrogenation conditions are adjusted so that the content of dissolved oxygen in the carbohydrate feed immediately prior to contacting with the catalyst is less than 0.5 ppm. The hydrogenation catalyst may be for example a ruthenium catalyst. The carbohydrate may be a monosaccharide, such as glucose or mannose, for example. It was found that the use of feeds which had a low dissolved oxygen content resulted in substantially increased lifetime of the hydrogenation catalysts through the reduction of gluconic acid in the spent catalyst. A temperature of 120° C. and a pressure of 2300 psig were used in the hydrogenation of glucose.

U.S. Pat. No. 5,162,517, Bayer Aktiengesellshaft (published Nov. 10, 1992) discloses a process for the preparation of an epimer-free sugar alcohol selected form the group consisting of xylitol, sorbitol (D-glucitol), 4-O-β-D-galactopyranosyl-D-glucitol (lactitol) and 4-O-α-D-glucopyranosyl-D-sorbitol (maltitol) by continuous catalytic hydrogenation of the corresponding sugar selected from D-xylose, α-D-glucose, 4-O-β-D-galactopyranosyl-α-D-glucopyranose (lactose) or 4-O-α-D-glucopyranosyl-α-D-glucopyranose (maltose). The hydrogenation is carried out at a hydrogenation pressure of 150 to 500 bar and at a temperature of 60 to 125° C. by a fixed bed process using hydrogenation catalysts in the form of carrier-free moldings. The hydrogenation catalyst comprises one or more elements of the iron group of the Periodic Table of Elements (iron, cobalt and/or nickel). Regarding the hydrogenation temperature of 60 to 125° C., it is recited that lower temperatures would not achieve a substantially quantitative conversion of the sugar, whereas higher temperatures lead to uncontrollable side reactions such as caramelization, ether splitting or destructive hydrogenation, these possibly resulting in discoloration and the formation of harmful by-products.

U.S. Pat. No. 6,124,443, Bayer Aktiengesellshaft (published Sep. 26, 2000) discloses a process for the preparation of the same sugar alcohols as above by continuous catalytic hydrogenation of the corresponding sugars at a hydrogen pressure of 100 to 400 bar and at a temperature of 20 to 70° C. The hydrogenation catalyst comprises one or more elements of the iron group of the periodic table alloyed with elements of subgroup IV and/or subgroup V. Regarding the hydrogenation temperature of 20 to 70° C., it is recited that the hydrogenation temperature should be as low as possible to decrease the energy costs.

U.S. Pat. No. 6,570,043 B2, Battelle Memorial Institute (published on Sep. 19, 2002) discloses a process of converting a sugar to a sugar alcohol by catalytic hydrogenation at a temperature less than 120° C., preferably at a temperature of 90 to 120° C. and at a pressure of 100 to 3000 pounds per square inch gauge hydrogen gas overpressure. The catalyst comprises ruthenium on a titania support. The starting sugar may be glucose or lactose, for example. It is recited that high conversion and good product selectivity are obtained by the use of a low processing temperature.

L. Fabre et al. describe the catalytic hydrogenation of arabinonic acid and arabinonolactones in Catalysis Communications (2001), 2(8), p. 249-253. Aqueous solutions of arabinonic acid in equilibrium with the corresponding γ-lactone and δ-lactone were hydrogenated to arabitol in a batch reactor in the presence of a ruthenium catalyst supported on active carbon. Introduction of small amounts of sodium anthraquinone-2-sulfonate decreased the reaction rate, but increased the selectivity from 93.6% to 97.9%. It is also recited that the presence of these molecules, which remain adsorbed on the catalyst surface even after successive recycling of the catalyst, decreased markedly the rate of dehydroxylation reactions leading to unwanted deoxy-products.

U.S. Pat. No. 6,486,366 B1, Degussa A G (published Nov. 26, 2002) discloses a method for producing alcohols by reacting a carbonyl compound in a catalytic hydrogenation reaction with hydrogen or hydrogen-containing gases in the presence of a Raney nickel catalyst, which is in the form of hollow bodies. Particularly preferred embodiments of the method relate to the production of sorbitol from dextrose, a mixture of sorbitol and mannitol from fructose, xylitol from xylose, maltitol from maltose, isomaltitol from isomaltose, dulcitol from galactose and lactitol from lactose. It is recited that pH can be adjusted with acid compounds like sugar acids, sorbic acid or citric acid. Furthermore, it is recited that in a continuous process it is also possible to conduct the hydrogenation in two or more steps. In this two-step process, the hydrogenation can be carried out in a first step at a temperature in the range between 60 and 90° C. and can be completed in a second step at a temperature from 90 to 140° C.

Regarding the hydrogenation of lactose to lactitol, the prior art does not disclose the formation of lactobionic acid as a by-product in the lactose hydrogenation process. Consequently, the prior art does not disclose or suggest any means to overcome the problems relating to the formation of aldonic acids, such as lactobionic acid and xylonic acid in the hydrogenation of the corresponding aldose to alditol e.g. due to the high hydrogenation temperature.

BRIEF DESCRIPTION OF THE INVENTION

It is an object of the present invention to provide an improved process for the catalytic hydrogenation of a sugar to the corresponding sugar alcohol so as to alleviate the above disadvantages, such as the deactivation and unstability of the catalyst and the problems relating to the recovery and regeneration of the catalyst, which relate to the formation of harmful by-products. These harmful by-products normally have a deactivating effect on the catalyst and shorten the catalyst lifetime by adhering to the catalyst surface. Especially, the invention relates to an improved process of hydrogenating ketoses and aldoses to corresponding alcohols, such as alditols, for example lactose to lactitol. The objects of the invention are achieved by a novel hydrogenation process, which is disclosed in the independent claim. The preferred embodiments of the invention are disclosed in the dependent claims.

The invention is based on reducing the interference of harmful by-products, such as aldonic acids in the catalytic hydrogenation of a sugar to a sugar alcohol by adjusting the hydrogenation conditions during the hydrogenation so as to maintain the catalyst activity and to prevent the formation of aldonic acids from aldoses and ketoses and to prevent the leaching and reprecipitation of the catalyst components during the hydrogenation. By applying the process of the invention, the catalyst can be effectively used in successive hydrogenations and can be easily recovered for example by filtration. With the process of the invention, a high conversion of the starting sugar and a high selectivity of the produced sugar alcohol, such as lactitol is achieved.

BRIEF DESCRIPTION OF THE DRAWINGS

The following drawings are illustrative examples of the invention and are not meant to limit the scope defined in the claims in any way. The standard lactose (40 w-% in deionized water) hydrogenation conditions were 120° C. and 50 bar over 10 w-% (dry content 50%) of sponge nickel catalyst, if not stated otherwise.

DEFINITIONS RELATING TO THE INVENTION

Figure 1:
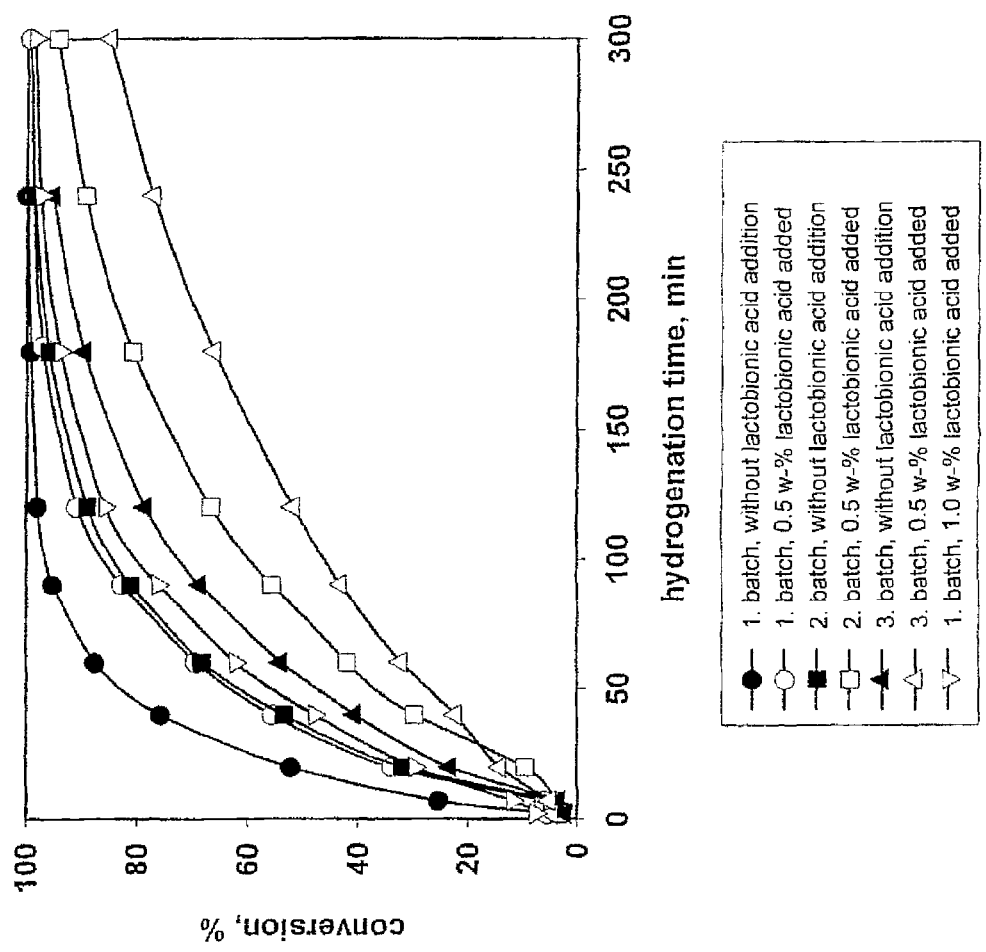
FIG. 1 shows the effect of lactobionic acid on the hydrogenation of lactose (conversion of lactose to lactitol as a function of the reaction time at various lactobionic acid concentrations).

"Temperature ramping" in connection with the present invention refers to the adjustment of the hydrogenation temperature so that the hydrogenation is started at a lower temperature, followed by gradual rising of the hydrogenation temperature to the final hydrogenation temperature.

"Pressure ramping" in connection with the present invention refers to the adjustment of the hydrogenation pressure so that the hydrogenation is started at a lower pressure, followed by gradual rising of the pressure to a desired hydrogenation pressure.

"Aldonic acids" in connection with the present invention refer to carboxylic acids derived from sugars (mono-, di- and trisaccharides). Typical examples of aldonic acids in connection with the present invention are lactobionic acid, xylonic acid, gluconic acid, mannonic acid and maltobionic acid.

"Conversion" in general refers to the consumption of the starting material (the starting sugar), expressed in percentage values.

"Selectivity" refers to the proportion of the desired sugar alcohol produced to all reaction products produced from the starting sugar, expressed in percentage values.

DETAILED DESCRIPTION OF THE INVENTION

The invention relates to a process for the catalytic hydrogenation of a sugar to the corresponding sugar alcohol. The process comprises adjusting the hydrogenation conditions to maintain the catalyst activity during consecutive hydrogenations so that the content of the corresponding aldonic acid of the sugar on the catalyst surface is low.

In the process of the present invention, the content of the aldonic acid on the catalyst is typically in the range of less than 3%, preferably in the range of less than 2% and more preferably in the range of less than 1%, calculated on the weight of the catalyst. The weight of the catalyst typically refers to the wet weight (50% dry content) of the catalyst.

The hydrogenation conditions are typically adjusted so as to maintain a high concentration of hydrogen on the catalyst surface during the hydrogenation, i.e. the hydrogenation conditions are adjusted so that the catalyst surface remains rich in hydrogen.

The catalysts ability to adsorb hydrogen may be determined by so-called temperature programmed desorption method (TPD). The method was carried out as follows:

Catalyst samples (fresh catalyst and recycled catalyst) were first dried for four hours at 130° C. by continuously flowing carrier gas (Ar) through the catalyst layer to remove all moisture. After drying the catalyst samples, hydrogen adsorption was performed either at room temperature or at 120° C. (lactose hydrogenation temperature) for 90 minutes. After adsorption, free hydrogen was flushed away with argon for 45 minutes. The TPD heating rate was 10° C./min from room temperature to 400° C. The analyses of the desorbed gases were carried out continuously with a quadrupole mass spectrometer.

TPD of hydrogen was performed by the method described above for a fresh Raney nickel sample (Activated Metals & Chemicals Inc. USA) and for a corresponding recycled catalyst sample (which had been used for 30 hours for lactose hydrogenation and washed with water after that). The uptake (desorption) of hydrogen in this example at 25° C. was 20.4 ml $H_2$/g catalyst ($9.1 \times 10^{-4}$ mol $H_2$/g catalyst) for a fresh catalyst and 16.7 ml/g catalyst ($7.6 \times 10^{-4}$ mol $H_2$/g catalyst) for a recycled catalyst. At 120° C., the uptake of hydrogen was 19.9 ml $H_2$/g catalyst ($8.9 \times 10^{-4}$ mol $H_2$/g catalyst) for a fresh catalyst and 11.3 ml $H_2$/g catalyst ($5.0 \times 10^{-4}$ mol/g catalyst) for a recycled one. The results show that lactobionic acid had accumulated on the surface of the recycled catalyst, which resulted in the decreased capacity of the recycled catalyst to adsorb hydrogen.

The sugar to be hydrogenated in accordance with the present invention is typically selected from mono-, di- and trisaccharides. In a preferred embodiment of the invention, the sugar is selected from aldose and ketose sugars. The aldose sugars are hydrogenated to corresponding alditols. Ketoses, such as fructose are hydrogenated to corresponding C2-alditol epimers. Typical examples of aldose sugars in connection with the present invention are lactose, glucose and xylose, which are hydrogenated to lactitol, sorbitol and xylitol respectively. The corresponding interfering aldonic acids formed during the hydrogenation of aldose sugars, such as lactose, glucose and xylose are lactobionic acid, gluconic acid and xylonic acid, respectively. Furthermore, other raw materials which contain aldoses and ketoses may be used as starting materials for the hydrogenation. These include invert sugars, isomerized glucose, glucose syrups, maltose syrups, fructose, tagatose, arabinose, ribose, isomaltulose, mannose, erythrose and galactose, for example.

In one embodiment of the invention, the hydrogenation conditions for maintaining the catalyst activity are adjusted by gradual heating of the hydrogenation solution.

In one aspect of this embodiment of the invention, the invention relates to a process for the production of a sugar alcohol from the corresponding sugar by catalytic hydrogenation, wherein the hydrogenation conditions are adjusted by introducing a sugar solution into a hydrogenation reactor at an initial hydrogenation temperature of 0 to 110° C., hydrogenating the sugar solution with simultaneous gradual heating of the solution to a final hydrogenation temperature in the range of 60 to 200° C., whereby the difference between the initial hydrogenation temperature and the final hydrogenation temperature is in the range of 100 to 20° C., and continuing the hydrogenation at the final hydrogenation temperature, until desired conversion of the sugar to the sugar alcohol is achieved.

In one embodiment of the invention, the temperature difference between the initial hydrogenation temperature and the final hydrogenation temperature is in the range of 80 to 20° C. and preferably 65 to 35° C.

In a further embodiment of the invention, the gradual heating is continued to a final hydrogenation temperature of 100° C. or more.

In the gradual heating, the heating is typically continued until a conversion of at least 40%, preferably more than 60% and most preferably more than 80% of the sugar to the sugar alcohol is achieved.

The initial hydrogenation temperature in the process of this aspect of the present invention is in the range of 0 to 110° C., preferably in the range of 50 to 100° C., for example in the range of 60 to 80° C.

The final hydrogenation temperature is in the range of 60 to 200° C., preferably 100 to 140° C.

The heating rate in the gradual heating is typically in the range of 0 to 5° C./min, more preferably 0.2 to 1.5° C./min, and most preferably 0.2 to 1° C./min.

The heating time in the gradual heating is typically in the range of 0.2 to 2.5 hours, more preferably 0.5 to 2 hours.

In one embodiment of this aspect of the invention, the heating rate may be faster at the beginning and slower at the end of the gradual heating or in opposite order.

In another embodiment of this aspect of the invention, the heating rate may be adjusted depending on the hydrogen consumption so that the hydrogen consumption will not rise to a too high level.

In another embodiment of the invention, the process may be further improved by adding a carboxylic acid or a salt thereof to the hydrogenation solution. The carboxylic acid is a small-molecular monocarboxylic acid typically selected from formic acid, acetic acid, propionic acid and benzoic acid. The amount of the carboxylic acid addition is typically in the range of 1 to 0.001 M, preferably 0.2 to 0.01 M into the sugar solution to be hydrogenated. The salt of the carboxylic acid may be selected from alkali metal salts, for example.

In one embodiment of the invention, the process comprises a combination of the gradual heating process and the addition of the small-molecular monocarboxylic acid described above.

The process of the present invention typically provides reduction of the formation of aldonic acids, such as lactobionic acid, xylonic acid and gluconic acid, which cause infererences in the hydrogenation of sugars to the corresponding sugar alcohols by deactivating the catalyst by adhering to the catalyst surface and by leaching the catalytic material compared to the hydrogenation process carried out at the same final temperature.

In the process of the present invention, the amount of the aldonic acid in the hydrogenation solution and on the surface of the hydrogenation catalyst is typically in the range of less than 2%, preferably less than 1% and most preferably less than 0.5%, calculated on the dry substance content of the hydrogenation solution and on the wet weight of the catalyst, respectively.

In a further embodiment of the invention, the process further comprises washing the catalyst with an alkali to regain the activity of the catalyst. The alkali is typically selected from NaOH and KOH. In a preferred regeneration process, the alkali wash is further followed by washing with water.

The catalyst useful in the process of the present invention is typically a metal catalyst where the metal is selected from groups 7, 8, 9, 10 and 11 of the Periodic Table of Elements. The catalysts useful in the present invention include iron, copper, cobalt, nickel, ruthenium, rhodium, palladium, osmium, iridium and platinum catalysts, for example. The catalysts may be used as such or they may be supported on an inert carrier. Suitable inert supports are for example alumina, silica, clays, titania and carbon. Sponge metal catalysts represent one useful catalyst type. Specific examples of useful catalysts are Raney nickel type as such or nickel metal on an inert support. The catalyst may also be promoted with e.g. Fe or Mo. In an especially preferred embodiment of the invention, the catalyst is selected from the group consisting of sponge nickel and supported nickel.

A typical catalyst load is in the range of 1 to 30% by weight, preferably 2 to 20% by weight of the initial sugar amount.

The pH of the hydrogenation is typically adjusted to a range of 4 to 10, preferably 5 to 7. If also epimerization is a target in the hydrogenation (like producing mannitol from glucose) slightly alkaline conditions can be used.

The hydrogenation is typically carried out at a pressure of 10 to 400 bar.

In one embodiment of the invention, the hydrogenation may be carried out in the presence of an organic solvent, such as an alcohol. The alcohol may be selected from ethanol and iso-propanol, for example.

By the process of the present invention, in the hydrogenation of the sugar to the corresponding sugar alcohol a conversion of more than 95%, preferably more than 99% and even up to 100% of the starting sugar may be achieved. The selectivity of the produced sugar alcohol is typically more than 95%, preferably more than 98% and even more than 99% of the converted sugar. Surprisingly high conversion and high selectivity are achieved with a rather short total reaction time despite the use of lower temperatures at the beginning of the process. Advantageously by the process of the invention, especially when using temperature ramping, over 90% of sugar is converted to the corresponding sugar alcohol after several consecutive hydrogenation batches in the reaction time shorter than without the temperature ramping. Saving in the hydrogenation time may be 10-20%. In the process of the present invention, the total hydrogenation time is typically 1 to 7 hours, preferably 2 to 5 hours.

Furthermore, appropriate mixing in the hydrogenation reactor is as a rule required to maintain the catalyst activity and to achieve high product selectivity.

The process of the invention may be carried out as a batch process or a continuous process. In a preferred embodiment of the invention, the process of the invention is carried out as a batch process.

In the following, the invention will be described referring to an embodiment where temperature ramping is used in the catalytic hydrogenation of lactose to lactitol.

A typical equipment for realizing the process of the present invention for the hydrogenation of lactose to lactitol comprises a hydrogenation feed tank for the starting lactose solution, a hydrogenation reactor for the hydrogenation reaction, means for introducing hydrogen into the hydrogenation reactor, means for introducing alkali to the hydrogenation reactor for controlling pH of the hydrogenation reaction, a catalyst preparation tank, a catalyst tank for the hydrogenation catalyst, filter units for the recovery of the catalyst, an intermediate tank for the lactitol product as well as the necessary piping, valves and heat exchangers. The hydrogenation process may be carried out as a batch process or a semi-batch process.

The starting lactose solution is typically pretreated before hydrogenation by filtration to remove undesired foreign substances. Before filtration, the pH of the lactose solution may be lowered by the addition of an acid, such as sulphuric acid to denature the proteins. After filtration, the lactose solution is typically subjected to ion-exchange treatment and treatment with activated carbon.

For the hydrogenation process, the lactose solution pretreated as above is introduced into the hydrogenation reactor provided with appropriate mixing device. The pH of the reaction solution is controlled by the addition of alkali, such as dilute sodium hydroxide to the hydrogenation reactor. Hydrogen may be added to the top or to the bottom of the hydrogenation reactor. Furthermore, the necessary catalyst is introduced into the hydrogenation reactor. The hydrogenation reactor may be for example a so-called loop reactor consisting of the actual hydrogenation reactor and a heat exchanger, whereby the hydrogenation process involves circulation of the reactor content in the loop formed by the hydrogenation reactor and the heat exchanger. Gradual heating can be carried through with heat exchangers. When the hydrogenation batch is terminated, the reactor pressure and temperature are reduced. The reactor content is transferred to an intermediate tank. From the intermediate tank the solution is transferred to the catalyst filters for the catalyst removal. The catalyst may be transferred to the catalyst recycle vessel for reuse in the next hydrogenation batch. The process may be carried out as a batch or semi-batch process.

The lactitol solution is then purified by conventional methods, such as ion-exchange and carbon treatments.

The purified lactitol solution is crystallized in a conventional way, for example by cooling crystallization. The crystalline lactitol is separated from the mother liquor. The crystalline lactitol thus obtained is dried in a lactitol dryer, size-classified (for example on a screener) and packaged.

By the use of temperature ramping (a low temperature at the beginning of the hydrogenation reaction) in accordance with the present invention, the conversion rate at the beginning of the hydrogenation reaction was maintained at an essentially constant level. Several advantages were achieved by using the temperature ramping, when compared to the hydrogenation of using the same final temperature for the whole hydrogenation time. It was found that the temperature ramping effectively reduced the formation of lactobionic acid in the hydrogenation of lactose to lactitol. The deactivation of the catalyst through lactobionic acid was thus reduced or eliminated. The catalyst remained rich in hydrogen resulting in reduced formation of lactobionic acid and reduced leaching of nickel and aluminium from the catalyst and an increased catalyst lifetime when using sponge nickel as the hydrogenation catalyst. The recovery of the catalyst by filtration was easier as formation of lactobionic acid decreased.

Furthermore, it was found that the use of temperature ramping improved the lactitol selectivity. Besides lactobionic acid, the amount of other by-products, such as lactulitol, galactitol and sorbitol was reduced. Furthermore, pH dropped down more slowly when temperature ramping was used, which has also the advantage of decreased alkali consumption.

The use of temperature ramping had also the advantage that the time to complete the hydrogenation reaction was short. Furthermore, temperature ramping also saved energy, because less energy was needed in the beginning of the batch and the total reaction time was shorter.

Furthermore, the use of temperature ramping has a favourable effect on the crystallization of lactitol, because temperature ramping reduces the amount of by-products that disturb crystallization, such as galactitol.

The same equipment as described above may be also used for the embodiment of the invention which utilizes the addition of carboxylic acids. In the hydrogenation of lactose to lactitol, it was found that the addition of acetic acid, benzoic acid, formic acid and propionic acid into the reaction solution slowed down the formation of lactobionic acid, but did not slow down the conversion of lactose to lactitol.

The lactitol product obtained from the hydrogenation may be used for pharmaceutical or alimentary purposes.

As further embodiments of the invention, the hydrogenation process of the invention may be applied to the hydrogenation of glucose, xylose, mannose, maltose, fructose and isomaltulose to corresponding alditols. The use of temperature ramping in accordance with the present invention improves the hydrogenation of xylose to xylitol, whereby less xylonic acid and less arabinitol are formed. In the hydrogenation of glucose to sorbitol, less gluconic acid is formed. Moreover, in the hydrogenation of maltose, less maltobionic acid is formed.

Example 1

The Effect of Lactobionic Acid on the Hydrogenation of Lactose to Lactitol

Lactose (manufactured by Ault Foods) was dissolved in ion-exchanged water to obtain a lactose solution containing 40% lactose by weight. The lactose solution was introduced into a hydrogenation reactor, which was a 300 ml batch reactor (Parr Instrument Co.) equipped with a concave blade impeller. The hydrogenation was carried out at 120° C. and at a hydrogen pressure of 50 bar with a mixing rate of 1800 rpm over sponge nickel catalyst (manufactured by Activated Metals). The catalyst load in the experiments was 10% by weight (dry substance content of 50% by weight) of the initial lactose amount.

Three consecutive batches were hydrogenated with the same catalyst without the regeneration of the catalyst, whereby 0.5% by weight of lactobionic acid (calculated on the total lactose solution) was added to the lactose solution before the start of hydrogenation. In the same way, three consecutive batches were hydrogenated as control tests without the addition of lactobionic acid. Furthermore, one batch was hydrogenated by adding lactobionic acid in an amount of 1% by weight with fresh catalyst. The hydrogenations were performed and the conversion of lactose to lactitol was monitored for a time period of 4-6 hours. The conversion results are shown in FIG. 1.

The conversion results show that lactobionic acid slows down the hydrogenation rate of lactose compared to tests without the addition of lactobionic acid. The deactivation of the nickel catalyst from batch to batch was clearly more significant when lactobionic acid was added.

Example 2

The Effect of Sequential Temperature Adjustments (Temperature Ramping)

A lactose solution was prepared in the same way as in Example 1. The equipment used for the hydrogenation as well as the hydrogenation pressure, the mixing rate, the catalyst and the catalyst dosage in the hydrogenation were the same as in Example 1. Three consecutive batches were hydrogenated with the same catalyst without any regeneration of the catalyst in the same way as in Example 1.

The hydrogenations were performed for 240 minutes. The temperature in the hydrogenation reactor was adjusted during the hydrogenation and varied in the tests as follows (in test 1, the whole hydrogenation was carried out at the same final temperature, whereas in tests 2 to 5 the hydrogenation was started at a lower temperature and the temperature was then rised gradually to the final hydrogenation temperature):

Test 1: the whole reaction was carried out at 120° C.
Test 2: temperature ramping from 90° C. to 120° C. during the first 30 minutes of the reaction (1° C./min).
Test 3: temperature ramping from 90° C. to 120° C. during the first 60 minutes (0.5° C./min).
Test 4: temperature ramping from 90° C. to 120° C. during the first 120 minutes (0.25° C./min).
Test 5: temperature ramping from 60° C. to 120° C. during the first 120 minutes (0.5° C./min).

Figure 2:
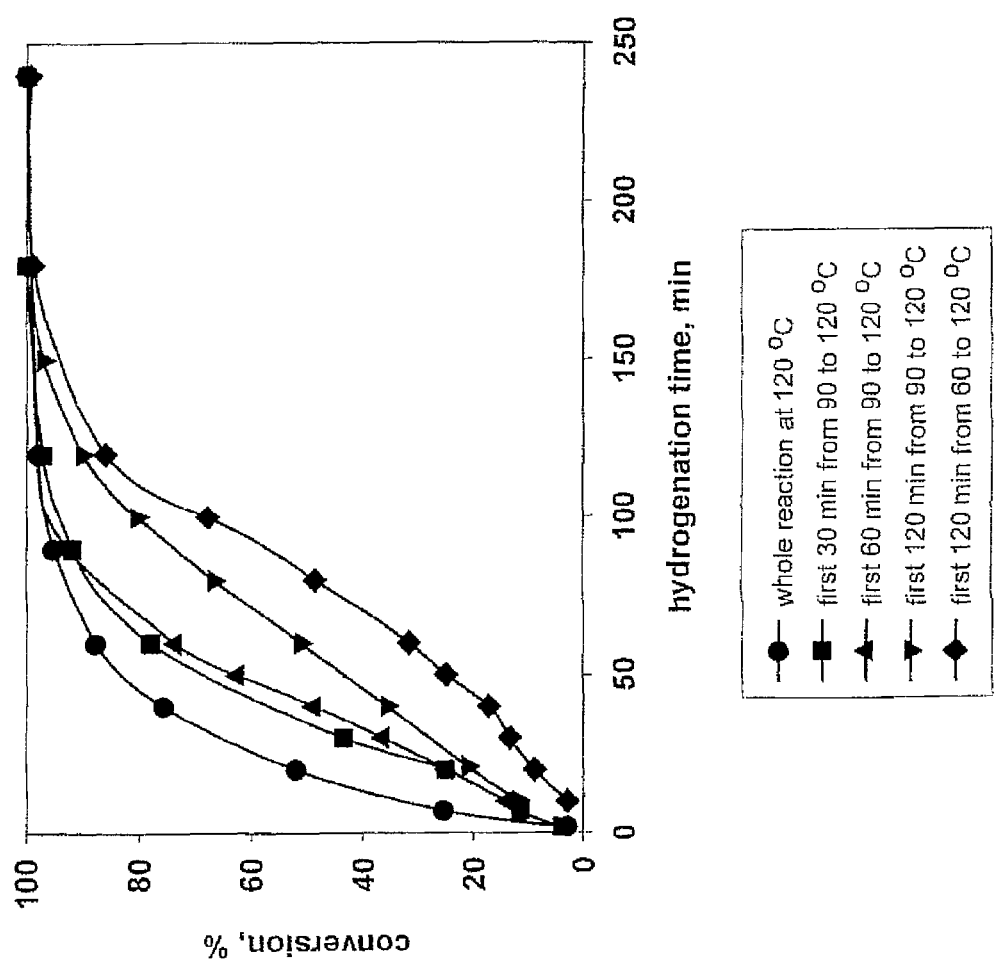
FIG. 2 shows the conversion of lactose to lactitol as a function of the reaction time at various hydrogenation temperatures (temperature ramping).
Figure 3:
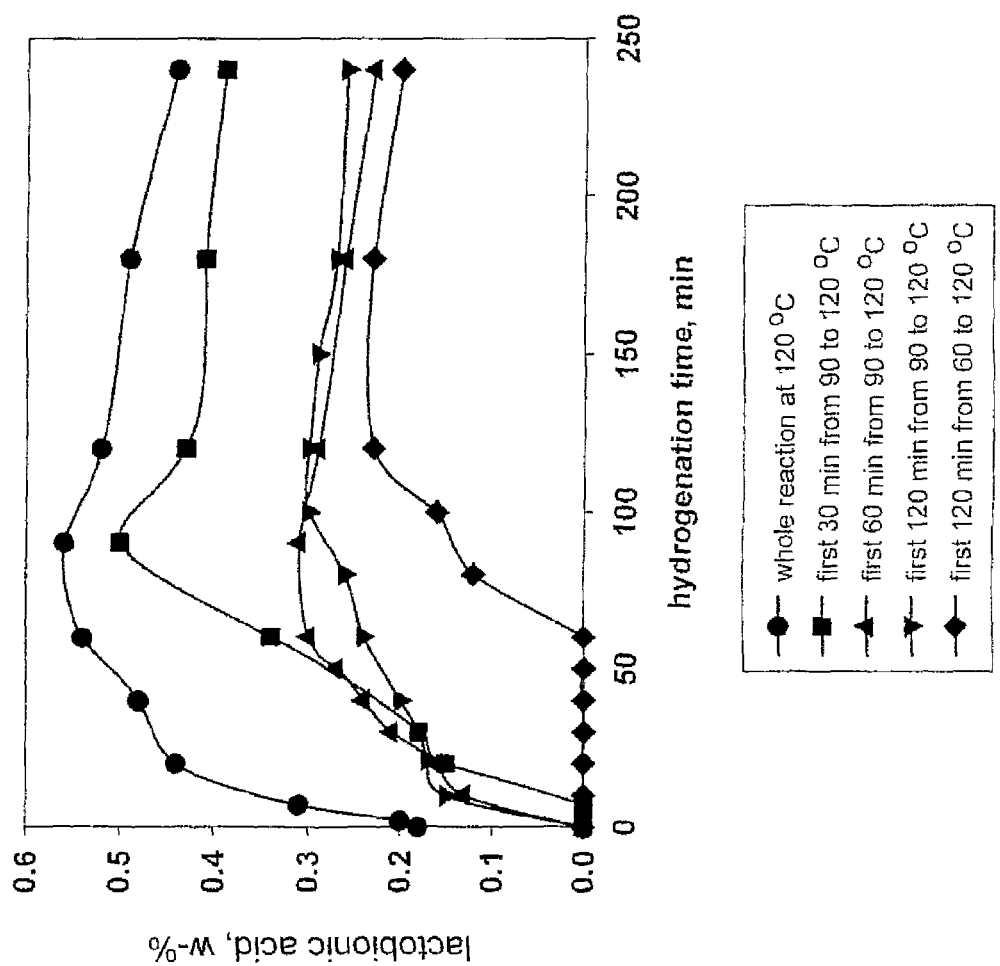
FIG. 3 shows the formation of lactobionic acid as a function of the hydrogenation time at various hydrogenation temperatures (temperature ramping).

The test results are shown in FIGS. 2 and 3. The results show the retarded and significantly lower production of lactobionic acid when the reaction was started at a lower temperature and the temperature was then rised slowly from 60° C. or 90° C. to 120° C. Despite the lower temperature during the first part of the hydrogenation, a high conversion degree of lactose to lactitol was achieved at the end the hydrogenation reactions. The conversion in the first batch was 100% and in the third batch 95 to 98%. With recycled catalysts, the conversion was higher when temperature ramping was used compared to the reaction without temperature ramping.

Furthermore, the following table 1 shows that temperature ramping clearly improved the hydrogenation selectivity.

TABLE 1

| Lactitol selectivity at 99% conversion level | |
|---|---|
| Hydrogenation conditions | Selectivity, % |
| The whole reaction at 120° C. | 97.35 |
| Temperature ramping (the first 30 minutes) from 90 to 120° C. | 98.90 |
| Temperature ramping (the first 60 minutes) from 90 to 120° C. | 98.95 |
| Temperature ramping (the first 120 minutes) from 90 to 120° C. | 99.30 |
| Temperature ramping (the first 120 minutes) from 60 to 120° C. | 99.40 |

Figure 4:
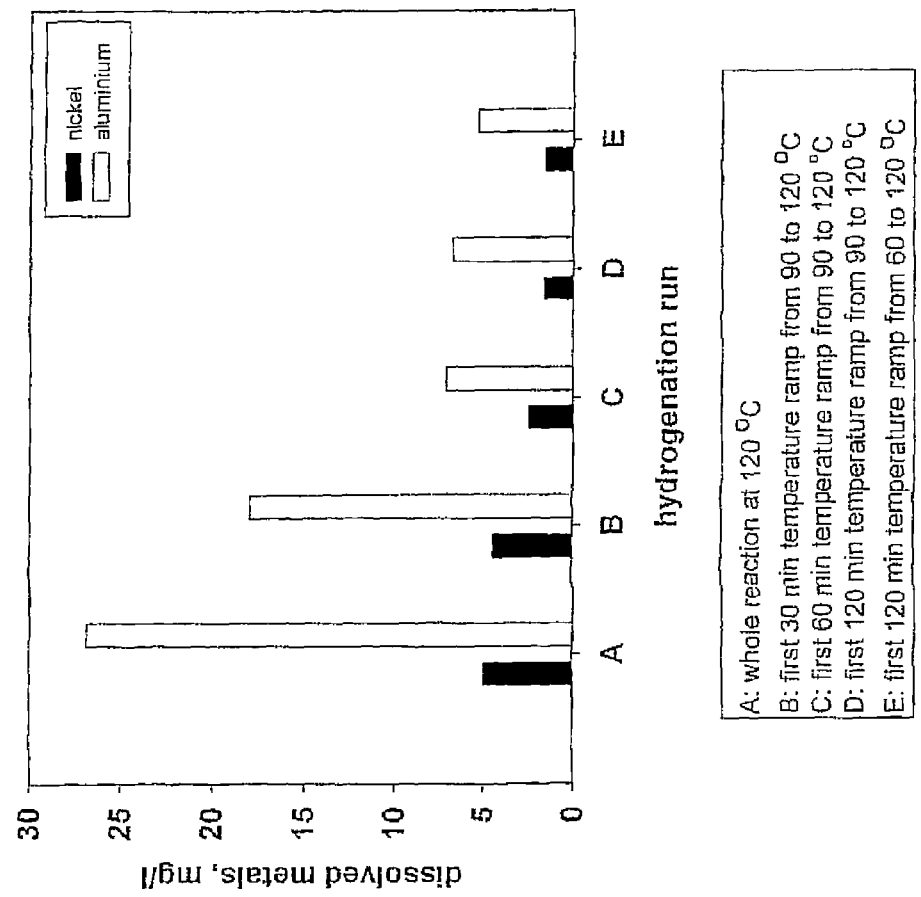
FIG. 4 shows the effect of temperature ramping on leaching of nickel and aluminium from the catalyst in the hydrogenation of lactose to lactitol.

Furthermore, FIG. 4 shows that temperature ramping significantly decreased leaching of nickel and aluminium from the catalyst compared to the test where the whole reaction was carried out at 120° C.

Example 3

The Effect of the Catalyst Amount on the Hydrogenation of Lactose

A lactose solution was prepared in the same way as in Example 1. The equipment used for the hydrogenation as well as the hydrogenation pressure, the mixing rate and the catalyst were the same as in Example 1. The hydrogenation was carried out with three different catalyst loadings of 5, 10 and 20% by weight of the catalyst (50% by weight of the dry substance content), calculated on the initial lactose amount. The hydrogenation time was 3 to 6 h. Hydrogenations were carried out without temperature ramping (the whole reaction was carried out at a temperature of 120° C.) or with temperature ramping from 90° C. to 120° C. (0.25° C./min) during the first 120 minutes of the reaction.

The results of the tests are shown in FIGS. 5 to 8. The results show that the following advantages were achieved by the use of temperature ramping in accordance with the present invention with all the catalyst dosage levels.

Figure 5:
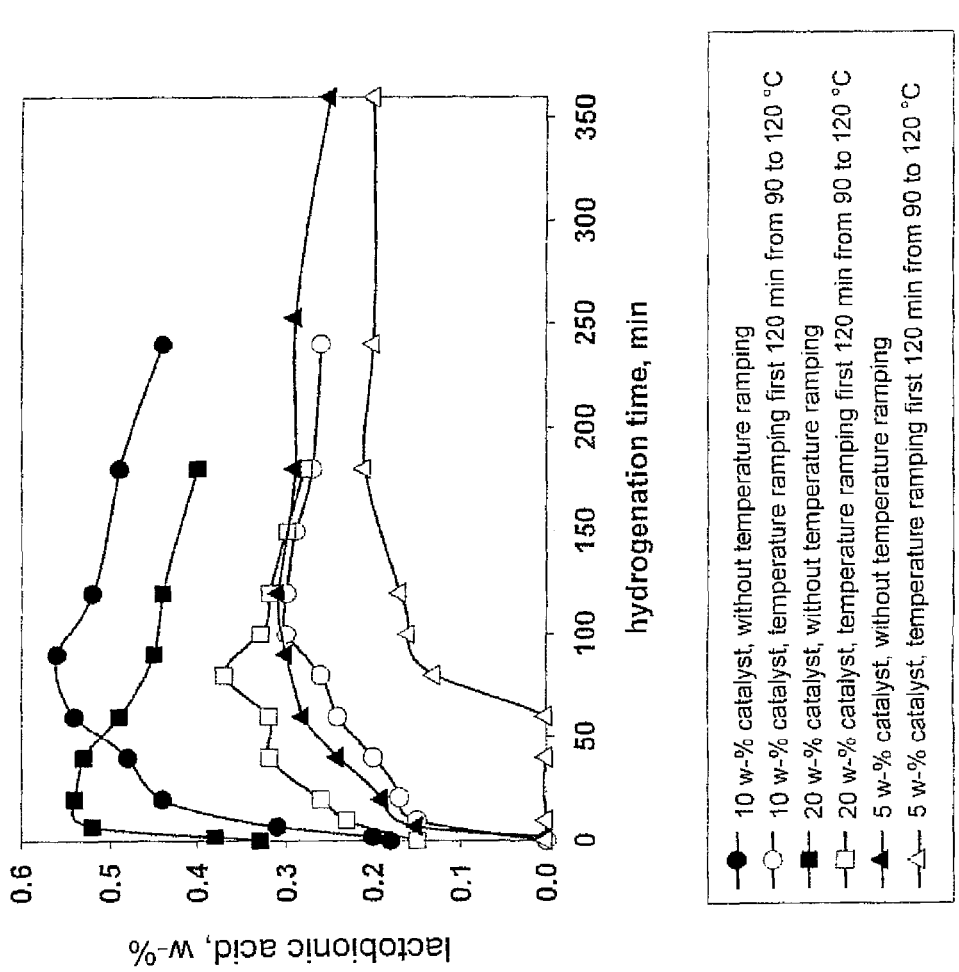
FIG. 5 shows the effect of temperature ramping and the catalyst amount on the formation of lactobionic acid as a function of the hydrogenation time.

FIG. 5 shows the reduced formation of lactobionic acid.

Figure 6:
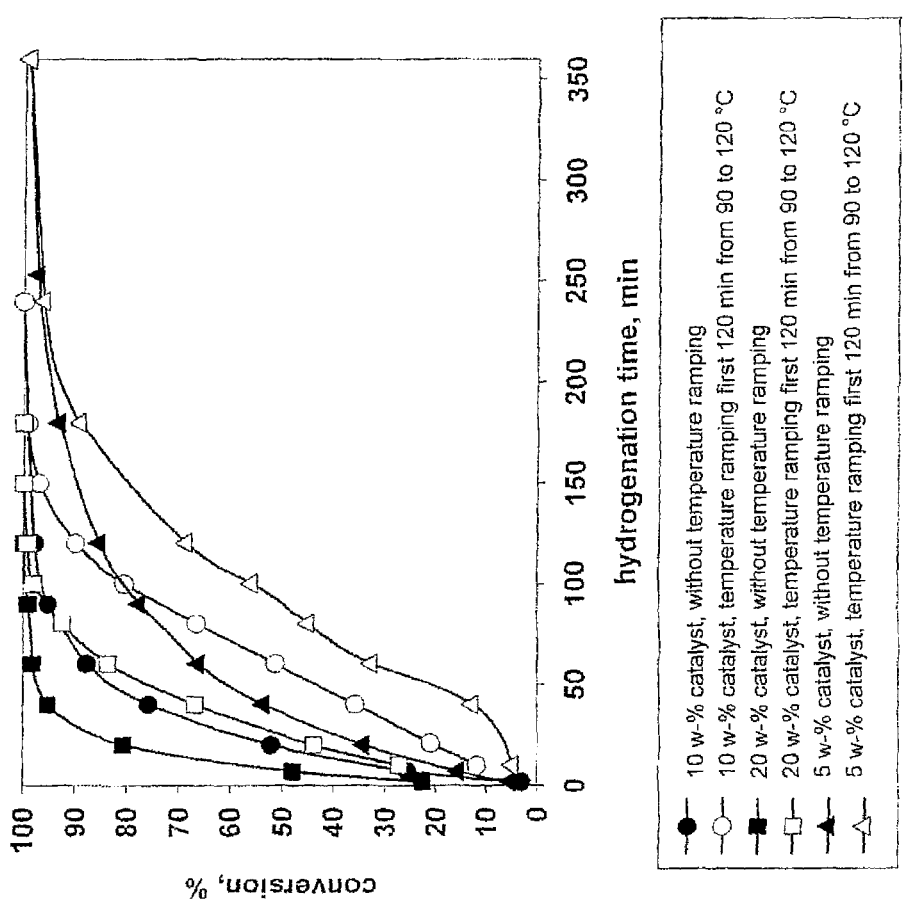
FIG. 6 shows the effect of temperature ramping and the catalyst amount on the reaction rate in the hydrogenation of lactose to lactitol.

FIG. 6 shows the excellent conversion of up to 100% of lactose to lactitol.

Figure 7:
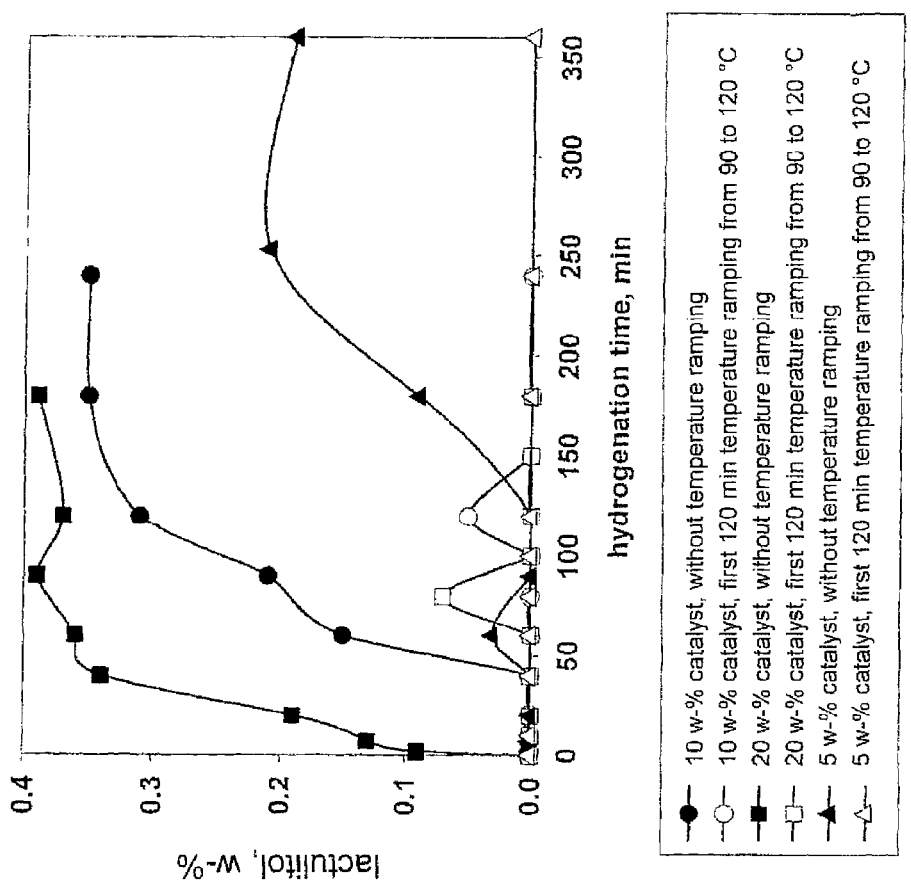
FIG. 7 shows the effect of temperature ramping on the formation of lactulitol as a function of the hydrogenation time with different catalyst amounts in the hydrogenation of lactose to lactitol.
Figure 8:
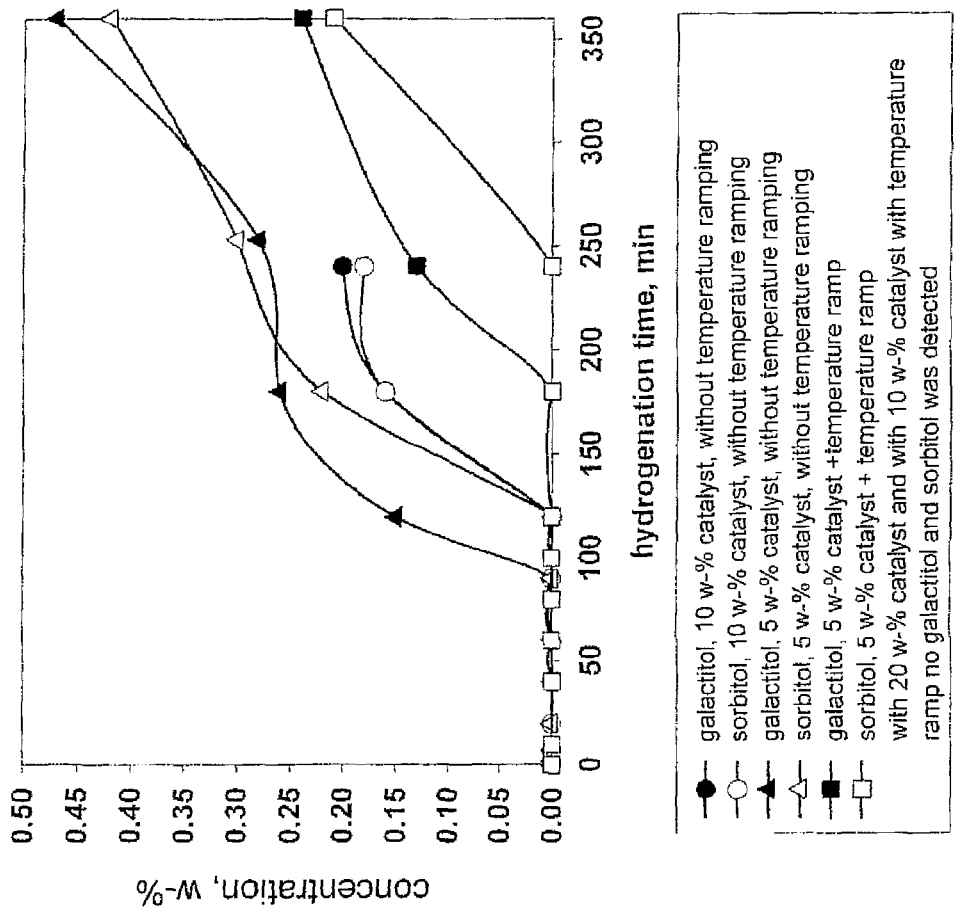
FIG. 8 shows the effect of temperature ramping on the formation of galactitol and sorbitol as a function of the hydrogenation time with different catalyst amounts in the hydrogenation of lactose to lactitol.

FIGS. 7 and 8 show the reduced amount of other by-products, such as lactulitol, sorbitol and galactitol.

Furthermore, the following table 2 also shows that excellent selectivity of lactose to lactitol was achieved.

TABLE 2

| Lactitol selectivity at 99% conversion level | |
| --- | --- |
| Hydrogenation conditions | Selectivity, % |
| No temperature ramping, 5% catalyst | 96.60 |
| Temperature ramping (the first 120 minutes) from 90 to 120° C., 5% catalyst | 98.40 |
| No temperature ramping, 10% catalyst | 97.35 |
| Temperature ramping (the first 120 minutes) from 90 to 120° C., 10% catalyst | 99.30 |
| No temperature ramping, 20% catalyst | 97.85 |
| Temperature ramping (the first 120 minutes) from 90 to 120° C., 20% catalyst | 99.20 |

Furthermore, it was found that the use of temperature ramping resulted in a slower pH drop and decreased leaching of the catalyst (nickel and aluminium) at each dosage level.

Example 4A

The Effect of the Hydrogenation Pressure on the Hydrogenation of Lactose

Lactose (manufactured by Leprino Foods) was dissolved in ion-exchanged water to obtain a lactose solution containing 40% lactose by weight. The hydrogenations were carried out at 120° C. at four different hydrogenation pressures (20, 35, 55 and 70 bar). The hydrogenation catalyst was a sponge nickel catalyst (manufactured by Acticat) and the catalyst load was 10% by weight (50% dry content).

Figure 9A:
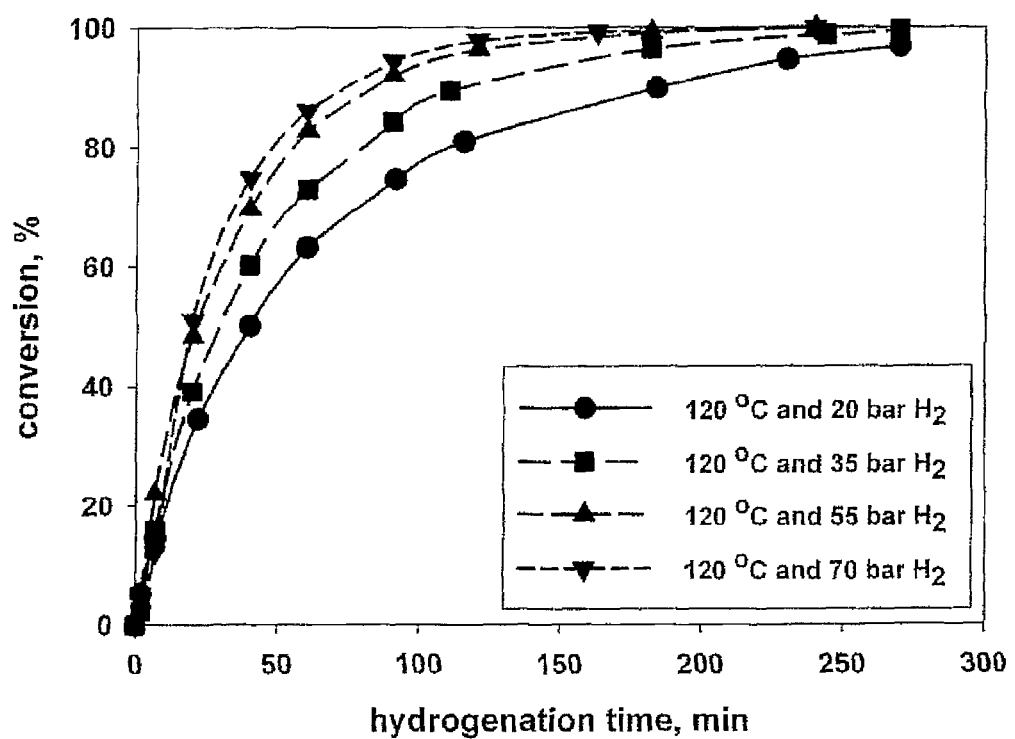
FIG. 9A shows the effect of the hydrogen pressure on the conversion of lactose to lactitol.
Figure 9B:
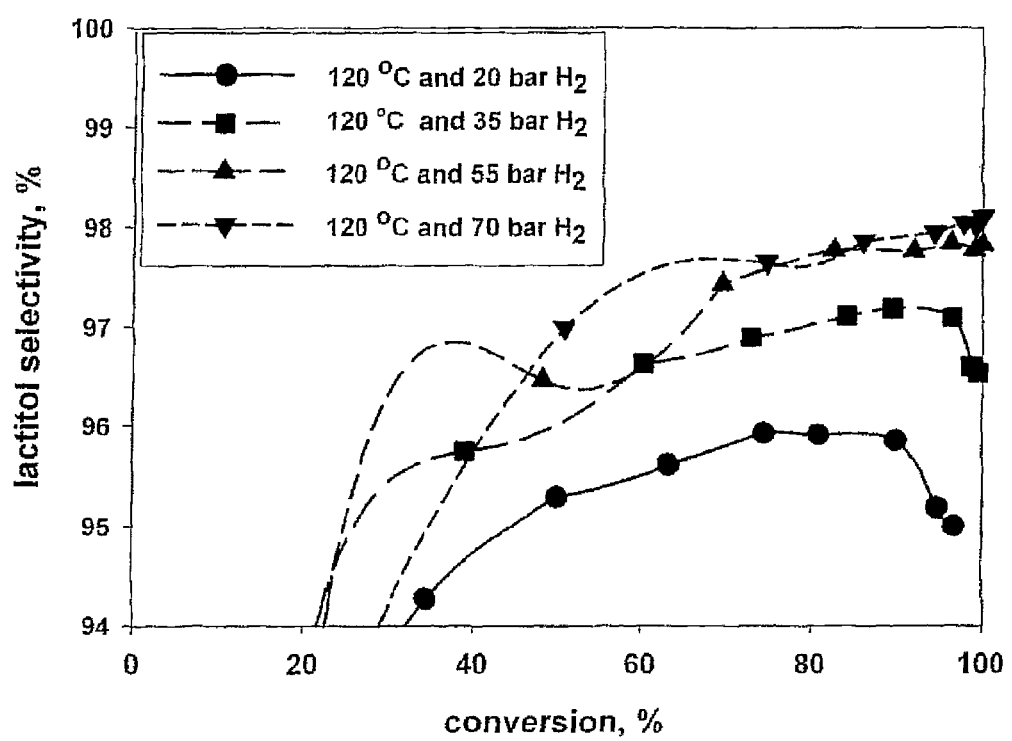
FIG. 9B shows the effect of the hydrogen pressure on lactitol selectivity.
Figure 9C:
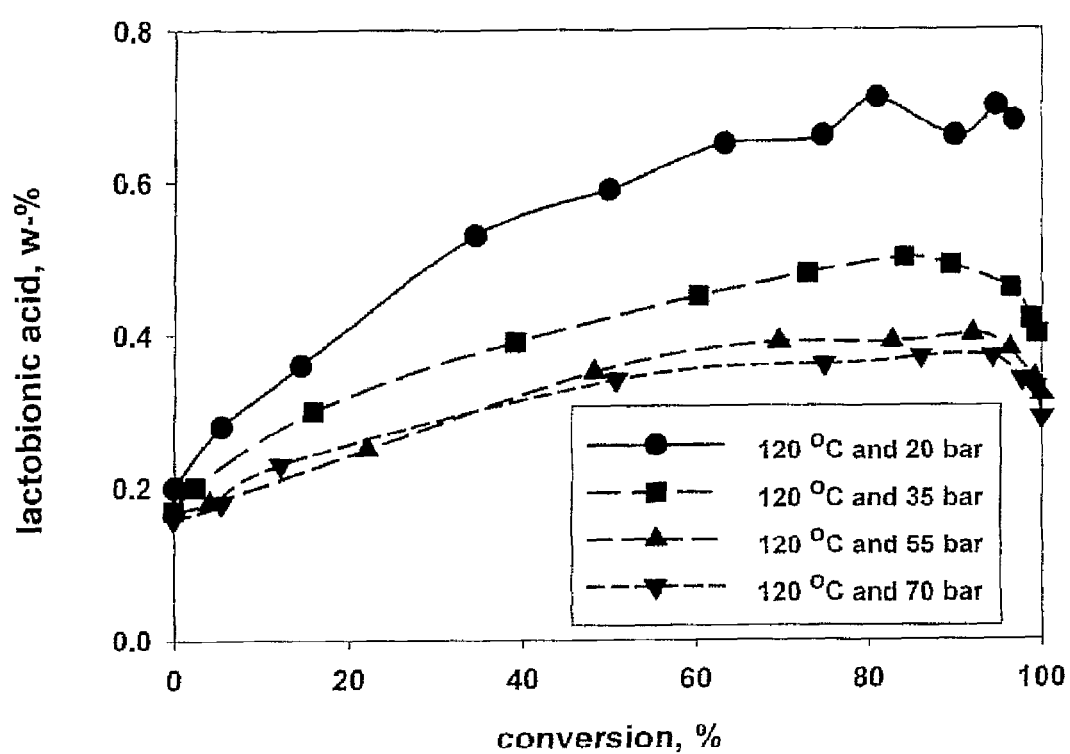
FIG. 9C shows the effect of the hydrogen pressure on the formation of lactobionic acid.

The hydrogenation results are shown in FIGS. 9A, 9B and 9C. FIG. 9A shows the influence of the hydrogen pressure on lactose conversion as a function of the hydrogenation time. FIG. 9B shows the influence of the hydrogen pressure on lactitol selectivity as a function of lactose conversion. FIG. 9C shows the influence of the hydrogen pressure on the formation of lactobionic acid as a function of lactose conversion.

The results of FIGS. 9A, 9B and 9C show that the formation of lactobionic acid formation increases during the lactose hydrogenation process, leading to decreased reaction rate and decreased lactitol selectivity, if the hydrogen pressure in the reactor is low.

Example 4B

The Effect of Sequential Pressure Adjustments (Pressure Ramping) on the Formation of Lactobionic Acid in the Hydrogenation of Lactose to Lactitol A lactose solution was prepared in the same way as in Example 1. The equipment used for the hydrogenation and the catalyst were the same as in Example 1. The lactose solution was hydrogenated at a temperature of 120° C. and at a hydrogen pressure of 50 bar. The catalyst dosage was 10% by weight (50% by weight of the dry substance) of the initial lactose amount. Three consecutive hydrogenation batches were carried out with the same catalyst. Hydrogenations were performed for 240 minutes. The pressure in the hydrogenation reactor was adjusted during the hydrogenation to show how insufficient hydrogen pressure and insufficient amount of hydrogen on the catalyst surface affects the hydrogenation reaction. Three tests were carried out as follows:

Test 1: the whole reaction was carried out at 120° C. and at a hydrogen pressure of 50 bar.

Test 2: temperature ramping from 90° C. to 120° C. at 50 bar during the first 30 minutes.

Test 3: pressure ramping from 20 bar to 50 bar (1 bar/min) at 120° C. for the first 30 minutes.

Figure 9D:
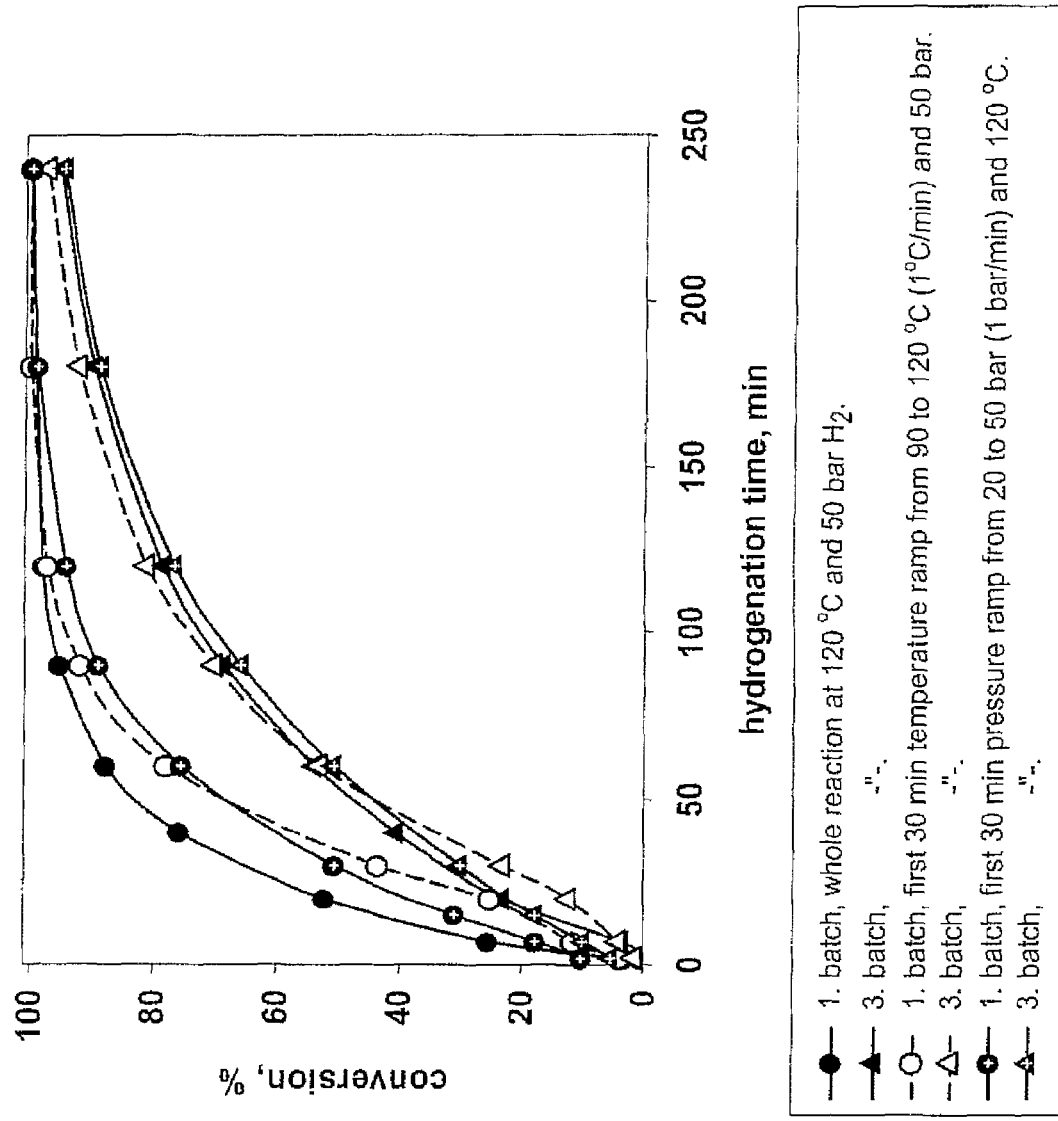
FIG. 9D shows the effect of temperature and pressure ramping on the conversion of lactose to lactitol.
Figure 10:
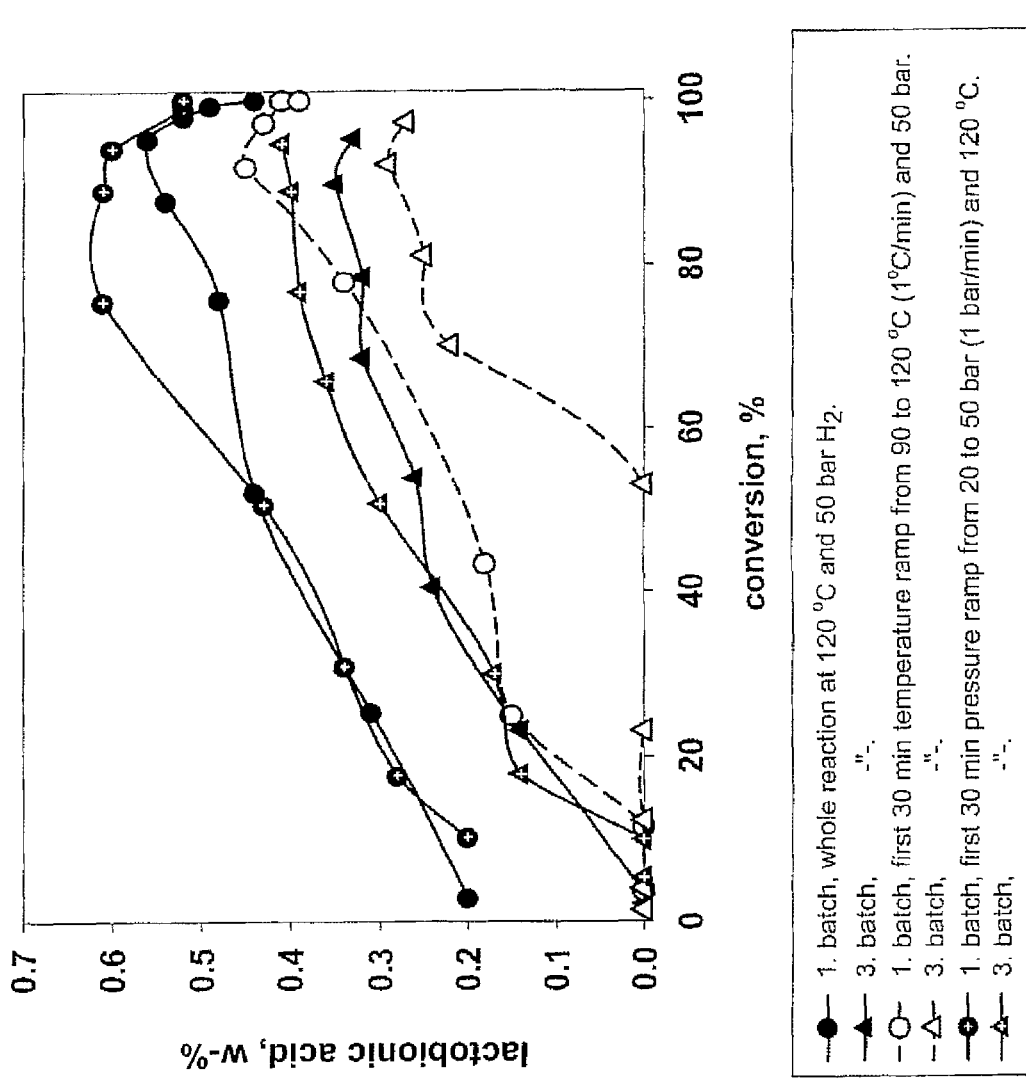
FIG. 10 shows the effect of the temperature and pressure ramping on the formation of lactobionic acid as a function of the conversion of lactose to lactitol.

The test results are shown in FIG. 9D. The results show the retarded conversion of lactose to lactitol when the pressure ramping from 20 bar to 50 bar during the first 30 minutes was in use. The effect was very similar when the temperature at the beginning of the hydrogenation reaction was rised gradually from 90° C. to 120° C. However, the formation of lactobionic acid in the process with the pressure ramping was even higher than in the process where the pressure was 50 bar during the whole hydrogenation process and clearly higher than in the process where the temperature ramping was in use (FIG. 10). The test results show that the formation of lactobionic acid will speed up when the hydrogen pressure is too low and the surface of the catalyst does not contain enough hydrogen.

The test results in FIG. 9 D also show that the use of temperature ramping improves conversion rate and the conversion of 90% in the third consecutive batch is achieved about 10% faster than without temperature ramping due to the lower formation of lactobionic acid.

Example 5

The Adsorption of Lactobionic Acid on the Catalyst Surface

The adsorption of lactobionic acid on the catalyst surface was studied by performing lactose hydrogenation batches at normal hydrogenation conditions, where the hydrogenation temperature was 120° C., the starting pH was 6.5 and the hydrogenation time was four hours. The lactose solution was prepared in the same way as in Example 1. The catalyst was a sponge type nickel catalyst. The amount of the catalyst was 7.5% wet catalyst per the lactose dry substance. Sodium carbonate was used as the buffer. Lactobionic acid was added to the second, third and fourth batch in an amount of 1, 2 and 3% by weight per the lactose dry substance before the reaction was started.

After the reaction, the catalyst (104 g wet weight) was separated from the product by filtration. The catalyst was rinsed by manual mixing with water (five minutes, 500 ml, lot A) and filtered again. The water was displaced from the catalyst, whereafter the adsorbed lactobionic acid was extracted from the catalyst using 1.0 N NaOH (350 ml, lot B), filtered and washed with water (350 ml, lot B) and filtered again. Lots A and B were combined, and the total amount of lactobionic acid adsorbed on the catalyst was analyzed from the combined lots (A+B). The results are shown in Table 3.

TABLE 3

The adsorption of lactobionic acid on the catalyst surface

|  | Batch 1 | Batch 2 | Batch 3 | Batch 4 |
|---|---|---|---|---|
| Acid added (g) (% on lactose) | 0 | 13.91 | 27.72 | 41.63 |
| Acid found adsorbed, % on wet weight of the catalyst | 0.8 | 0.7 | 0.6 | 0.5 |
| Acid formed in the solution (% on lactose) | 1.3 | 1.1 | 0.9 | 0.9 |

The results show that the amount of the lactobionic acid adsorbed on the catalyst was about the same order of magnitude irrespective of how much acid was added.

Example 6

Filtration of the Catalyst after the Reaction

Four hydrogenation batches were performed at a temperature of 120° C. for four hours at a starting pH of 6.5. The lactose solution for the hydrogenations was prepared in the same way as in Example 1. The catalyst and the amount thereof were the same as in Example 5. Sodium carbonate was used as the buffer. Lactobionic acid in an amount of 1, 2 and 3% per lactose dry substance was added to the second, third and fourth batch before the hydrogenation was started.

After the hydrogenation, filtration of the catalyst was carried out at a temperature of 70° C. with a flow rate of 50 ml/min using a sintered metal filter (0.5 μm), which had a filter size of 28.5 m². Three successive lots were filtered per batch. The filtration cake was replaced between the lots with water flush.

Figure 11A:
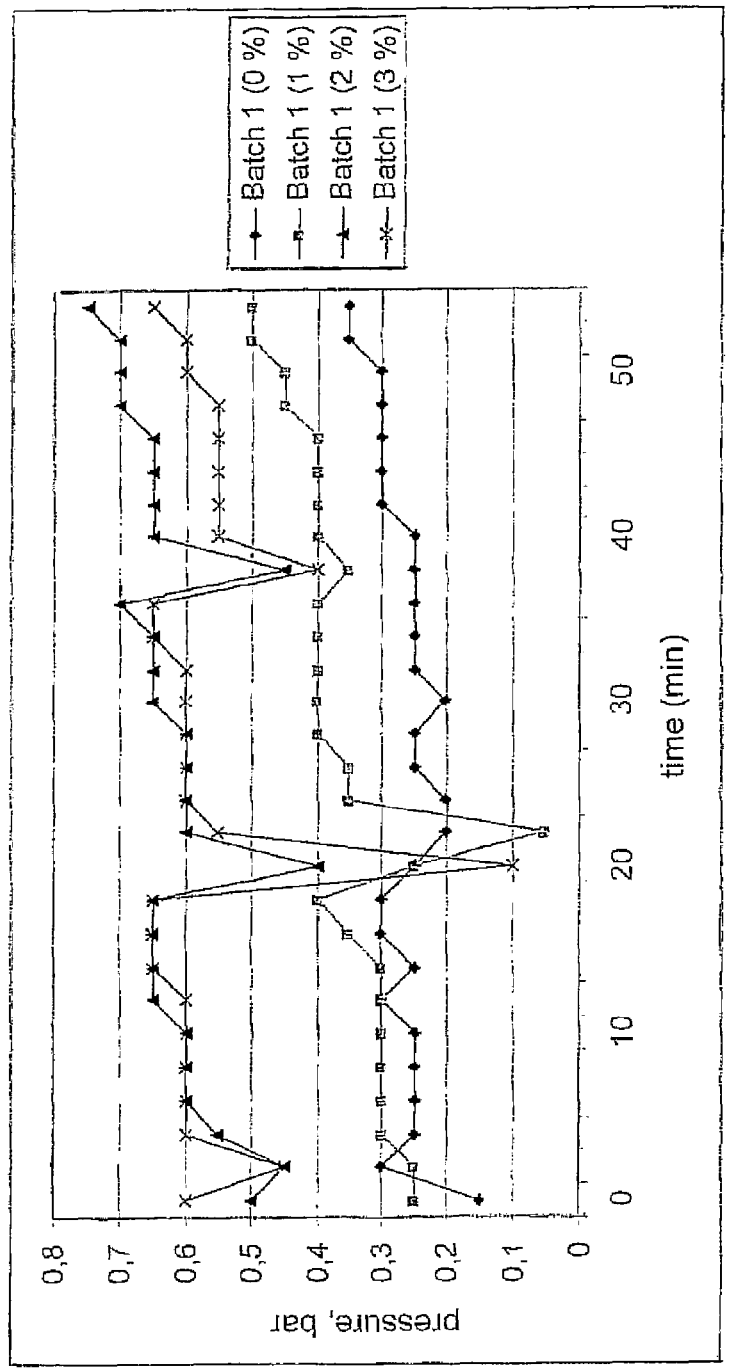
FIG. 11A shows the effect of added lactobionic acid on the pressure in the filtration of the catalyst.

The results of the filtration tests are presented in FIG. 11A, which shows the pressure versus filtration time over the filter with different amounts of added lactobionic acid. The results show that the pressure over the filter increases with increased amounts of added lactobionic acid.

Example 7

Regeneration of the Catalyst (A)

Five consecutive hydrogenation batches were performed with the same catalyst. A lactose solution (prepared in the same way as in Example 1) was hydrogenated at 120° C. and 50 bar. The amount of the catalyst was 10% by weight (50% by weight of the dry substance) of the initial lactose amount.

The catalyst regeneration was performed between the third and the fourth batch. Regeneration was carried out by washing the catalyst with NaOH solution (10% by weight) at 90° C. for two hours in the hydrogenation reactor. The stirring rate during the regeneration was 1000 rpm and nitrogen pressure of 5 bars was applied to the reactor to prevent the oxidation of the catalyst. After the NaOH wash, the catalyst was still washed with water for one hour at the same conditions.

It was found that alkali wash removed lactobionic acid from the catalyst surface in an amount of about 2%, calculated on the weight of the catalyst. The example thus shows that the catalyst activity was regained by alkali wash.

Regeneration of the Catalyst (B)

Figure 11B:
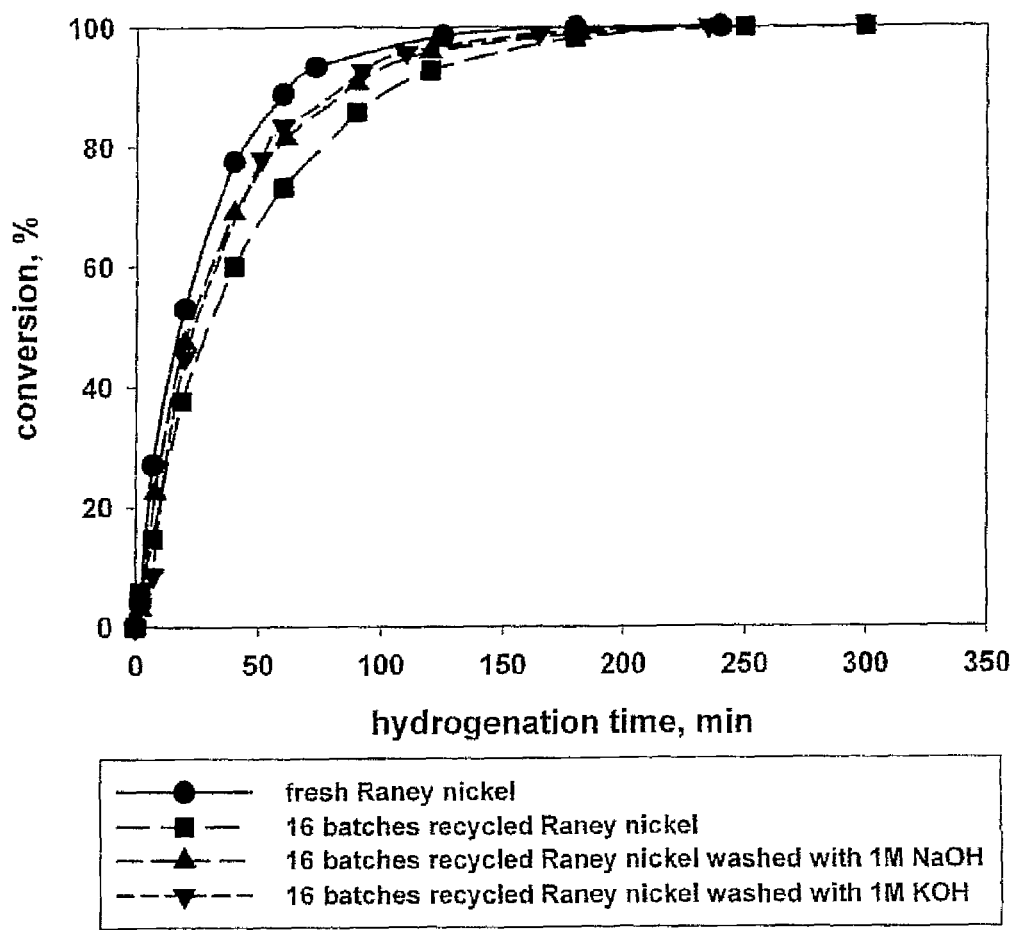
FIG. 11B shows the effect of the regeneration of the catalyst by alkali on the conversion of lactose to lactitol.

Hydrogenations were carried out with (1) fresh Raney Nickel®, (2) Raney Nickel® recycled in 16 hydrogenation batches without regeneration, (3) Raney Nickel® recycled in 16 hydrogenation batches and regenerated by washing with 1M NaOH as well as (4) Raney Nickel® recycled in 16 hydrogenation batches and regenerated by washing with 1M KOH. In the regenerations, the alkali washing was followed by repeated washing steps with water until the pH of the catalyst was 10. The results of the regeneration tests are shown in FIG. 11B. The results show that alkali wash removed aldonic acids thus regaining the catalyst activity.

Example 8A

The Effect of the Addition of Acetic Acid on the Formation of Lactobionic Acid

A lactose solution was prepared in the same way as in Example 1. The equipment used for the hydrogenation as well as the hydrogenation pressure, the mixing rate, the catalyst and the catalyst dosage in the hydrogenation were the same as in Example 1.

Hydrogenations were performed for 5 hours. 1.95 mmol acetic acid (corresponding to an amount of 0.084% by weight) was added to the lactose solution before the start of the hydrogenation. A control test was performed by adding the same molar amount (1.95 mmol) of lactobionic acid (corresponding to an amount of 0.5% by weight of lactobionic acid). The conversion of lactose to lactitol was monitored up to 300 minutes.

Figure 12:
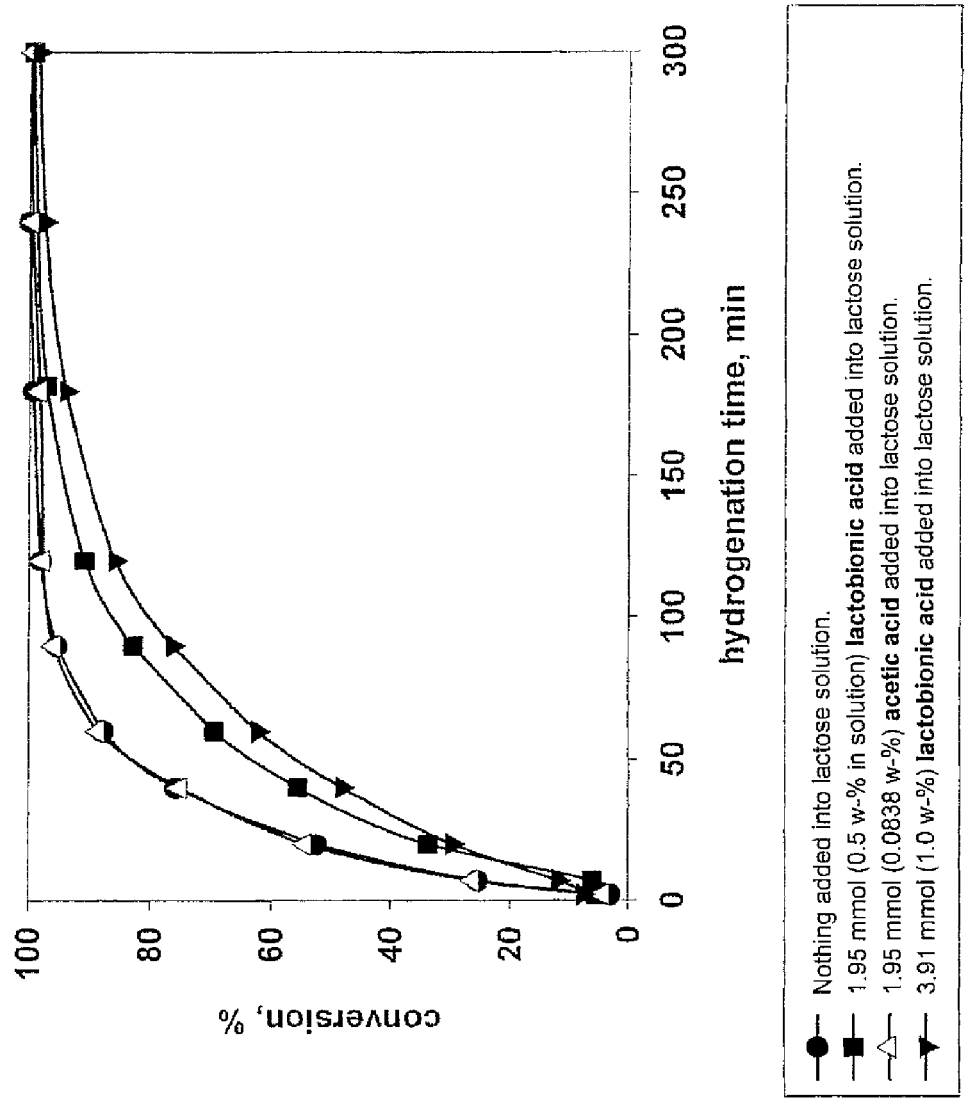
FIG. 12 shows the conversion of lactose to lactitol as a function of the hydrogenation time with the addition of acetic acid and lactobionic acid.
Figure 13:
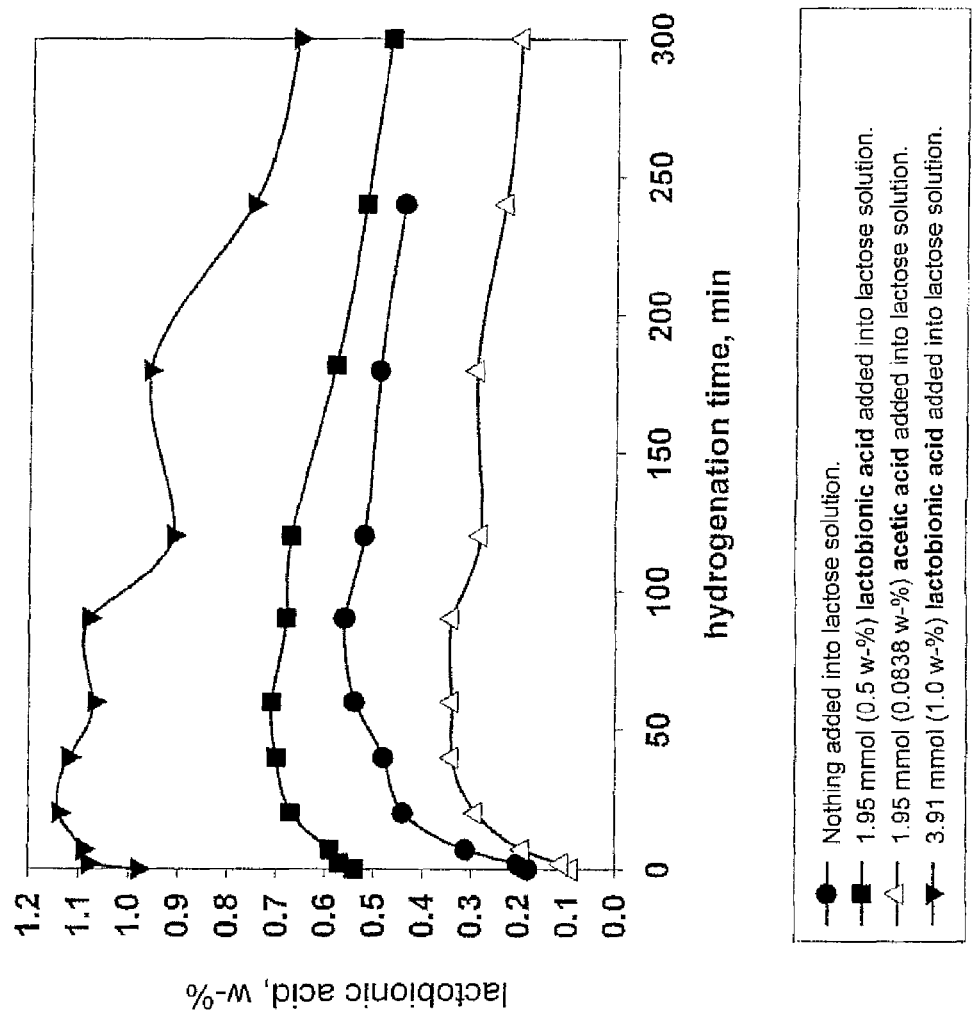
FIG. 13 shows the formation of lactobionic acid as a function of the hydrogenation time with the addition of acetic acid and lactobionic acid.

The results are presented in FIGS. 12 and 13. FIG. 12 shows the conversion of lactose to lactitol as a function of the hydrogenation time with the addition of acetic acid or lactobionic acid. FIG. 13 shows the amount of lactobionic as a function of the hydrogenation time with the addition of lactobionic acid or acetic acid. The conversion results of FIG. 12 show that the addition of acetic acid does not slow down the hydrogenation rate of lactose to lactitol as lactobionic acid did, whereas FIG. 13 shows that acetic acid slows down the formation of lactobionic acid during the hydrogenation. The addition of acetic acid also decreased catalyst leaching to some extent.

Example 8B

The Effect of the Addition of Acetic Acid and Various Other Carboxylic Acids on the Formation of Lactobionic Acid and Other by-Products Further experiments were carried out by adding acetic acid as well as some other carboxylic acids and salts thereof (benzoic acid, sodium benzoate, formic acid and propionic acid) into the hydrogenation batch prior to the beginning of the hydrogenation. The hydrogenations were performed with sponge nickel catalyst in the same way as in Example 8A.

Figure 14:
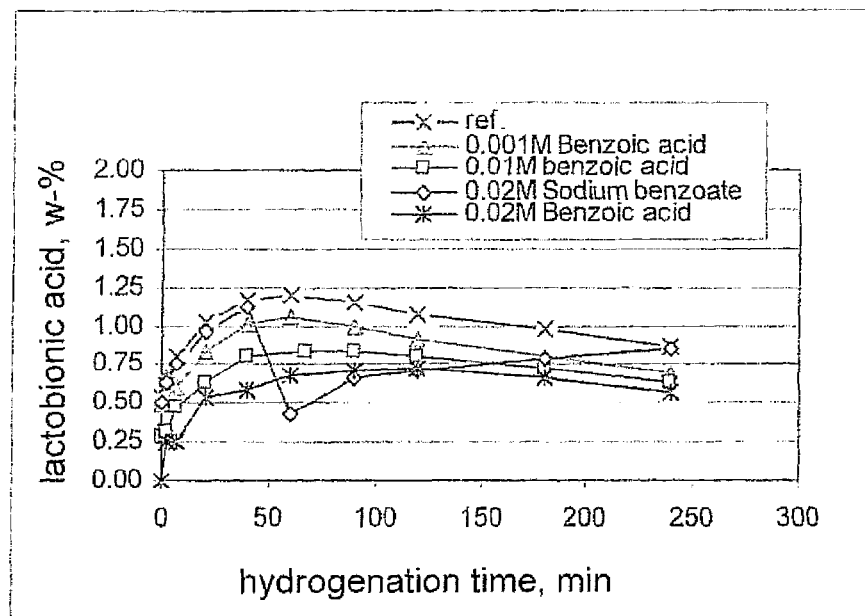
FIG. 14 shows the formation of lactobionic acid as a function of the hydrogenation time with the addition of benzoic acid and sodium benzoate.
Figure 15:
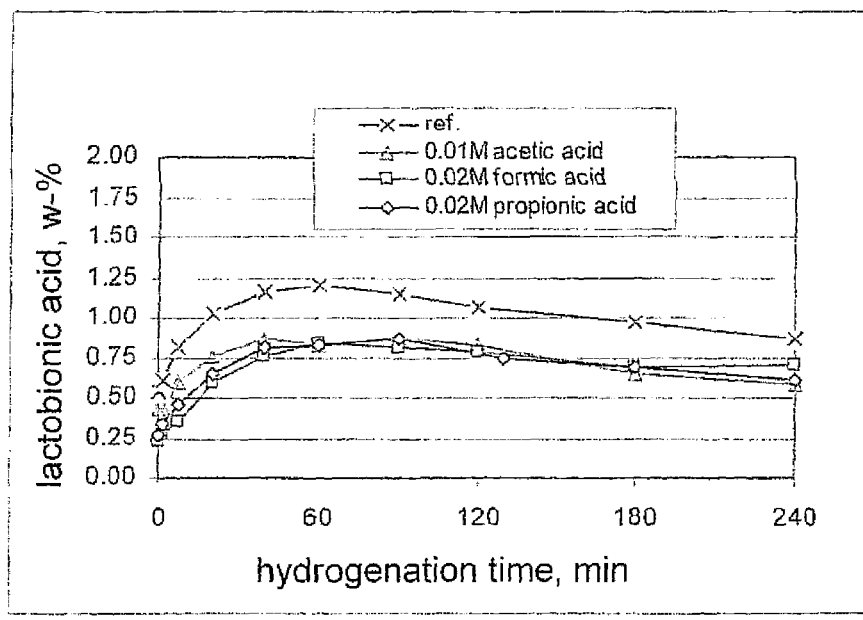
FIG. 15 shows the formation of lactobionic acid as a function of the hydrogenation time with the addition of acetic acid, formic acid and propionic acid.
Figure 16:
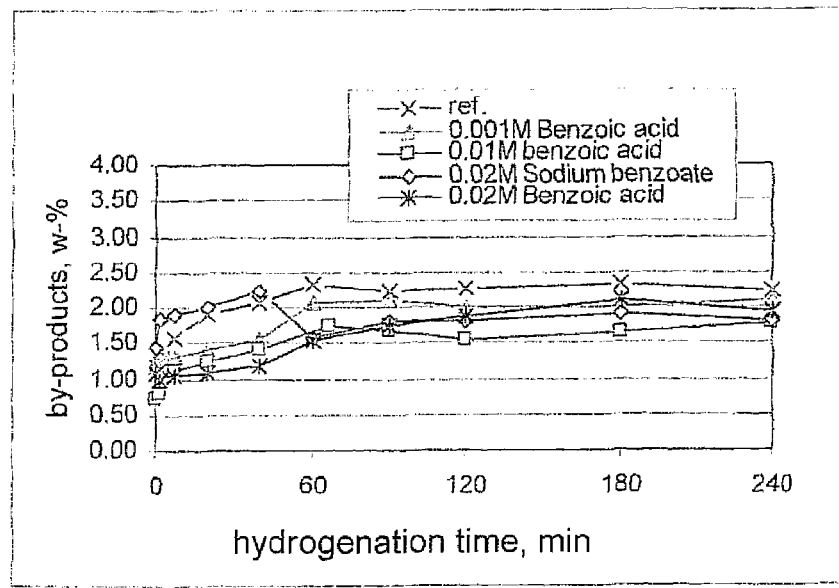
FIG. 16 shows the formation of by-products as a function of the hydrogenation time with the addition of benzoic acid and sodium benzoate.
Figure 17:
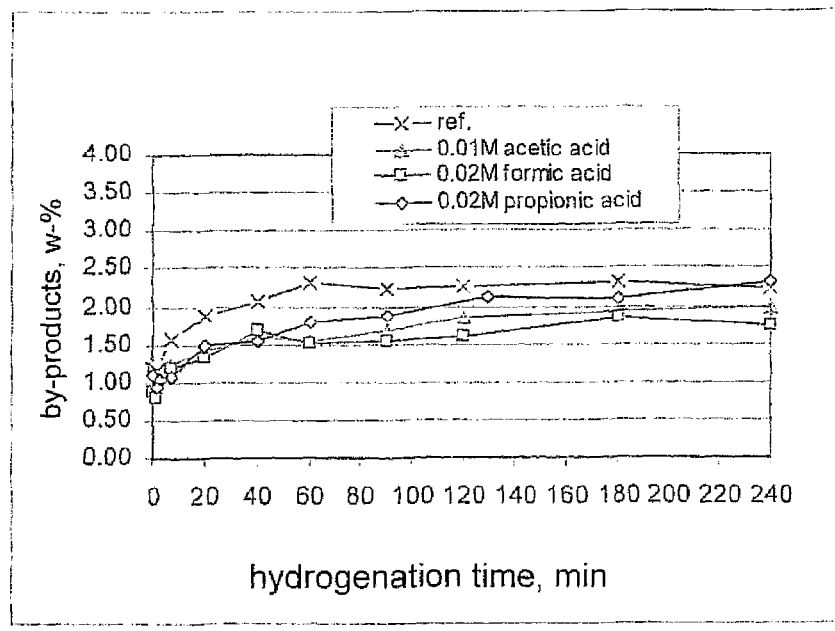
FIG. 17 shows the formation of by-products as a function of the hydrogenation time with the addition of acetic acid, formic acid and propionic acid.
Figure 18:
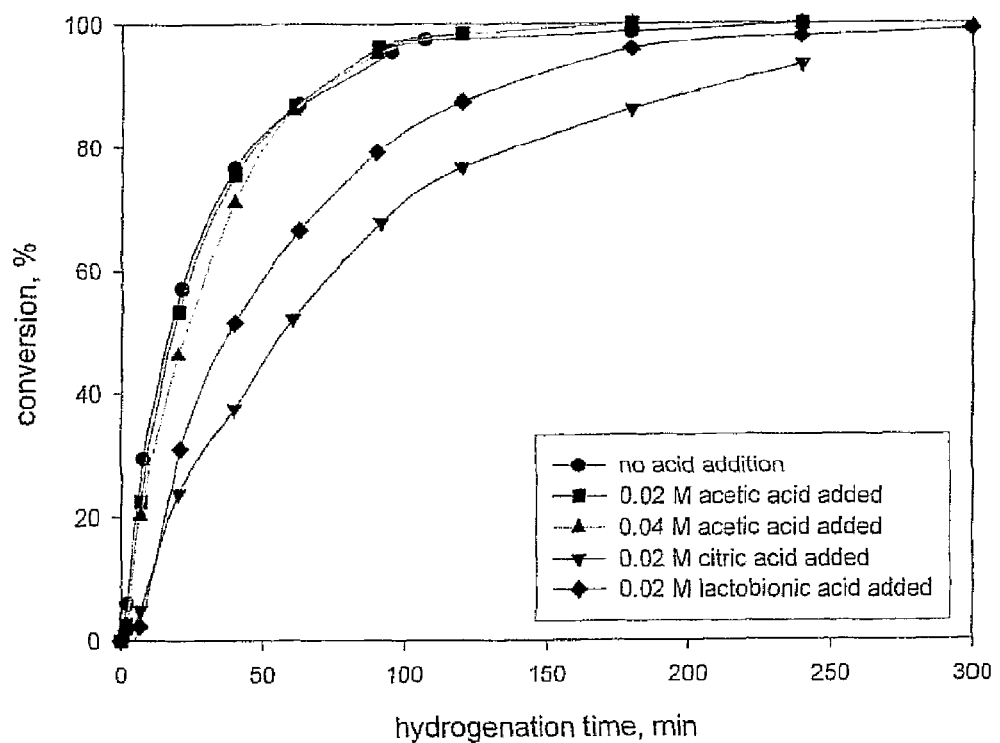
FIG. 18 shows the effect of the addition of acetic acid, citric acid and lactobionic acid on the conversion of lactose to lactitol.

The results are presented in FIGS. 14 to 18. FIG. 14 shows the effect of the addition of benzoic acid and sodium benzoate on the formation of lactobionic acid as a function of the hydrogenation time. FIG. 15 shows the effect of the addition of acetic acid, formic acid and propionic acid on the formation of lactobionic acid as a function of the hydrogenation time. FIG. 16 shows the effect of the addition of benzoic acid and sodium benzoate on the formation of by-products as a function of the hydrogenation time. FIG. 17 shows the effect of the addition of acetic acid, formic acid and propionic acid on the formation of by-products as a function of the hydrogenation time. FIG. 18 shows the effect of the addition of acetic acid, citric acid and lactobionic acid on the conversion of lactose to lactitol.

The results of FIGS. 14 to 17 show that the addition of benzoic acid, acetic acid, formic acid and propionic acid decrease the formation of lactobionic acid (FIGS. 14 and 15) and improve the product selectivity (FIGS. 16 and 17). FIG. 18 shows that the addition of acetic acid does not significantly influence the hydrogenation rate, whereas the addition of citric acid and lactobionic acid significantly decreased the hydrogenation rate.

Example 9

The Effect of Mixing on the Hydrogenation of Lactose

Lactose (manufactured by Leprino Foods) was dissolved in ion-exchanged water to obtain a lactose solution containing 40% lactose by weight. The hydrogenations were carried out at 120° C. and at a hydrogen pressure of 50 bar with three different mixing rates (600, 900 and 1800 rpm). The catalyst and the catalyst load were the same as in Example 1.

Figure 19:
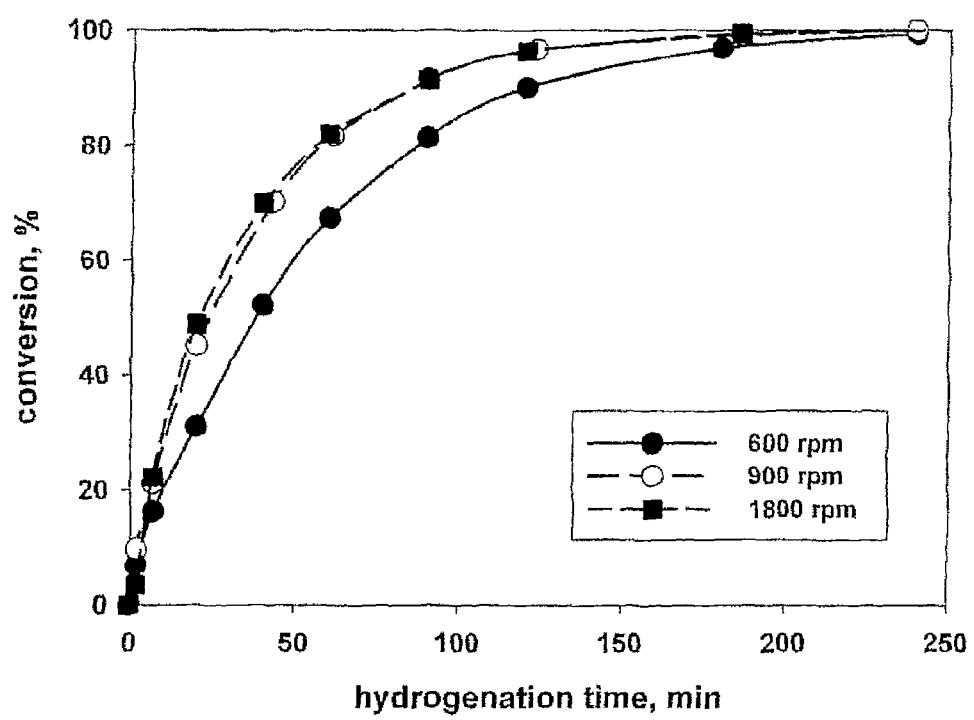
FIG. 19 shows the effect of mixing in the hydrogenation reactor on the conversion of lactose to lactitol.
Figure 20:
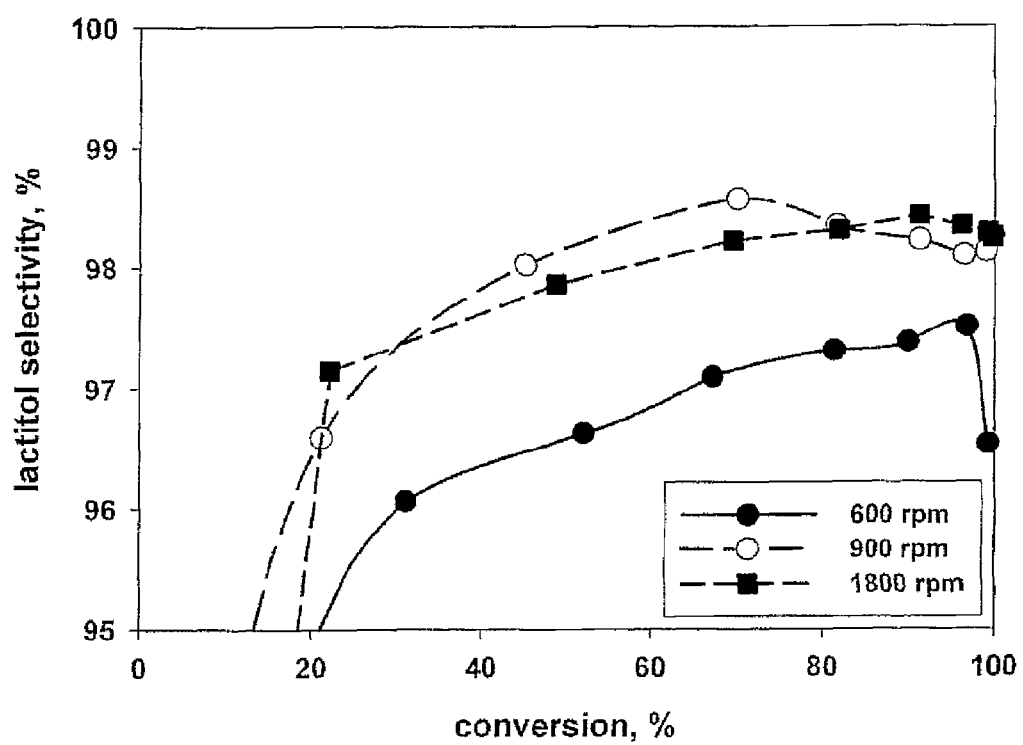
FIG. 20 shows the effect of mixing in the hydrogenation reactor on lactitol selectivity.
Figure 21:
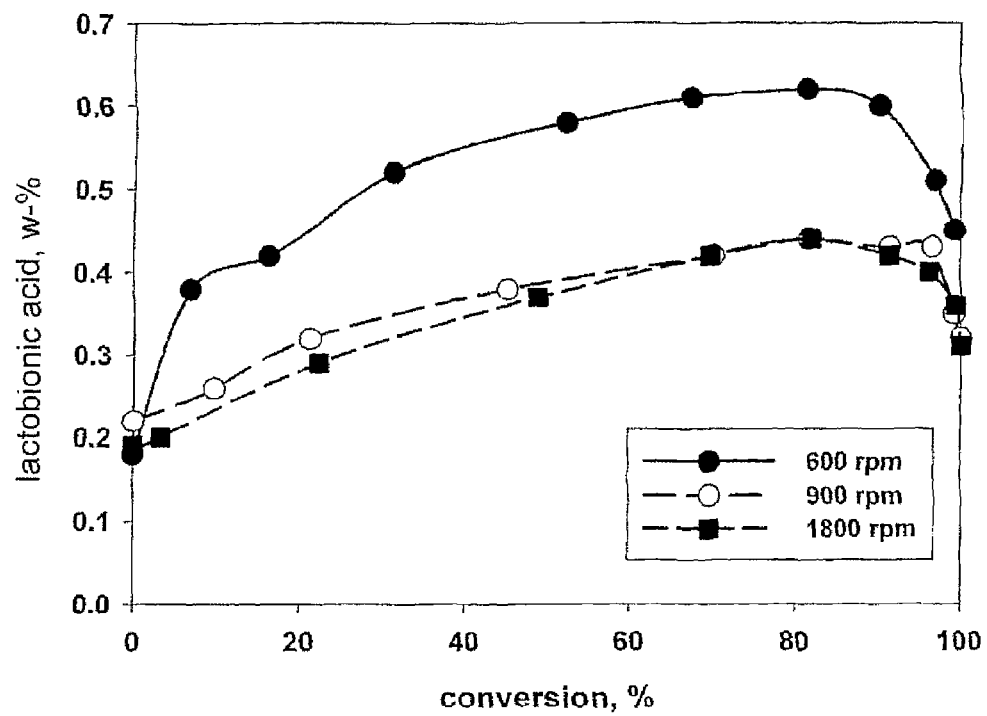
FIG. 21 shows the effect of mixing in the hydrogenation reactor on the formation of lactobionic acid.

The hydrogenation results are shown in FIGS. 19, 20 and 21. FIG. 19 shows the influence of the mixing rate on lactose conversion as a function of the hydrogenation time. FIG. 20 shows the effect of the mixing rate on lactitol selectivity as a function of lactose conversion. FIG. 21 shows the effect of the mixing rate on the formation of lactobionic acid as a function of lactose conversion.

The results show that lactobionic acid formation increases during the lactose hydrogenation process, leading to decreased hydrogenation rate and decreased lactitol selectivity, if mixing in the hydrogenation reactor is inefficient.

Example 10

The Effect of Xylonic Acid on the Hydrogenation of Xylose to Xylitol

A xylose solution (50% xylose by weight) was prepared by dissolving xylose in ion-exchanged water. The xylose solution was hydrogenated at a temperature of 110° C. and at a hydrogenation pressure of 50 bar with a mixing rate of 1800 rpm over sponge type Raney nickeltype catalyst (Activated Metals). The catalyst load was 5% by weight (dry substance content of 50%) of the initial xylose amount. The hydrogenation reactor was the same as in Example 1.

Hydrogenations were performed for 120 to 150 minutes. In one hydrogenation test series, 0.5% by weight of xylonic acid (calculated on the total xylose solution) was added to the xylose solution before the start of each hydrogenation batch. A control test was performed without the addition of xylonic acid. Five consecutive hydrogenation batches were performed with the same catalyst without regeneration of the catalyst. The conversion of xylose to xylitol was monitored up to 150 minutes.

Figure 22:
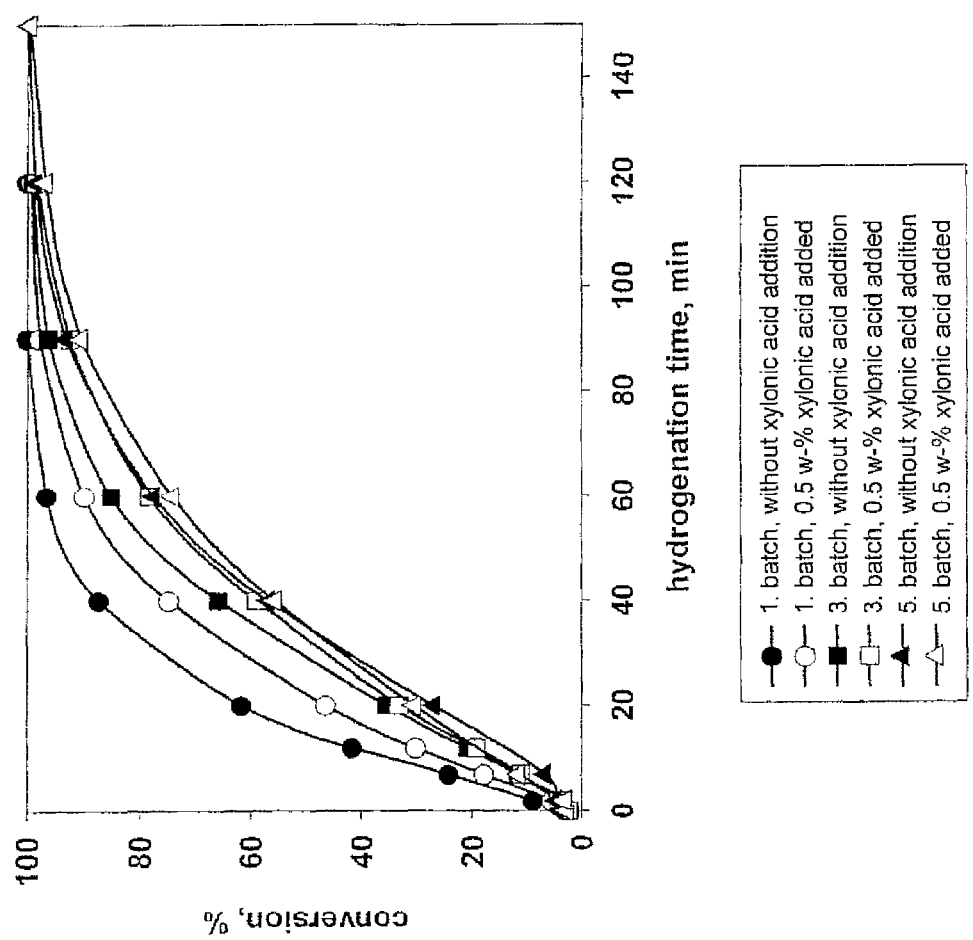
FIG. 22 shows the effect of xylonic acid on the conversion of xylose to xylitol in the hydrogenation of xylose (50 w-% in water) to xylitol at 110° C. and 50 bar over 5 w-% (dry content 50%) sponge nickel catalyst.

The conversion results are shown in FIG. 22. The results show that xylonic acid inevitably slows down the hydrogenation rate of xylose to xylitol compared to the tests without the addition of xylonic acid. The deactivation of the nickel catalyst from batch to batch was clear when xylonic acid was present. Furthermore, the addition of xylonic acid remarkably increased catalyst leaching.

Example 11

The hydrogenation of xylose to xylitol was made in agitated batch autoclave. Catalyst load was 7% of wet catalyst per xylose dry substance. Fresh wet catalyst (7% of the initial catalyst amount) was added to every third reaction to maintain the constant catalyst activity. Altogether 188 consecutive batches were made. In each batch hydrogenation temperature was first raised from 65° C. to 120° C. during 15 to 20 minutes and hydrogenation reaction time at 120° C. was 120 minutes. The xylose feed solution had xylose purity 99%/ds, dry substance content 50% and pH between 4 to 6. The amount of xylonic acid fixed on the catalyst during the hydrogenation was determined by eluting it with caustic from the catalyst samples taken from the reaction after batches 0, 5, 35, 106 and 188. The results are in the table 4.

TABLE 4

| Batch number | Xylonic acid (% of acid on wet catalyst) |
|---|---|
| 0 | 0.14% |
| 5 | 1.44% |
| 35 | 1.58% |
| 106 | 1.55% |
| 188 | 1.18% |

Xylonic acid amount on the catalyst surface is raising until the fifth batch and levelling out thereafter.

It will be obvious to a person skilled in the art that, as the technology advances, the inventive concept can be implemented in various ways. The invention and its embodiments are not limited to the examples described above but may vary within the scope of the claims.

The invention claimed is:

1. A process for catalytic hydrogenation of a sugar selected from the group consisting of lactose and xylose to the corresponding sugar alcohol, comprising subjecting the sugar to hydrogenation conditions that maintain catalyst activity during consecutive hydrogenations by limiting the content of aldonic acid selected from lactobionic acid, where lactose is the sugar, or xylonic acid, where xylose is the sugar, on the catalyst to less than 3% by wet weight of the catalyst, wherein the hydrogenation conditions comprise:
introducing a sugar solution into a hydrogenation reactor at an initial temperature of 50 to 100° C.,
hydrogenating the sugar solution by gradual heating of the solution at a heating rate in the range of 0.2 to 1.5° C./min to a final hydrogenation temperature in the range of 100 to 140° C., wherein the difference between the initial hydrogenation temperature and the final hydrogenation temperature is in the range of 80 to 20° C., and
continuing the hydrogenation at the final hydrogenation temperature until a conversion of the sugar to the sugar alcohol of more than 95% is achieved, whereby the content of lactobionic acid or xylonic acid on the catalyst is limited to less than 3% by wet weight of the catalyst.

2. A process as claimed in claim 1, wherein the content of the aldonic acid on the catalyst is less than 2% by wet weight of the catalyst.

3. A process as claimed in claim 1, wherein the content of the aldonic acid on the catalyst is less than 1% by wet weight of the catalyst.

4. A process as claimed in claim 1, wherein the sugar is xylose, the sugar alcohol is xylitol and the aldonic acid is xylonic acid.

5. A process as claimed in claim 1, wherein the difference between the initial hydrogenation temperature and the final hydrogenation temperature is in the range of 65 to 35° C.

6. A process as claimed in claim 1, wherein said gradual heating is continued until a conversion of at least 40% of the sugar to the sugar alcohol is achieved.

7. A process as claimed in claim 6, wherein said gradual heating is continued until a conversion of more than 60% of the sugar to the sugar alcohol is achieved.

8. A process as claimed in claim 7, wherein said gradual heating is continued until a conversion of more than 80% of the sugar to the sugar alcohol is achieved.

9. A process as claimed in claim 1, wherein the initial hydrogenation temperature is in the range of 60 to 80° C.

10. A process as claimed in claim 1, wherein said gradual heating employs a heating rate in the range of 0.2 to 1° C./min.

11. A process as claimed in claim 1, wherein said gradual heating is effected during a time period of 0.2 to 2.5 hours.

12. A process as claimed in claim 11, wherein said gradual heating is effected during a time period of 0.5 to 2 hours.

13. A process as claimed in claim 1, wherein the hydrogenation conditions to maintain the catalyst activity further comprise adding a small-molecular monocarboxylic acid or a salt thereof to the hydrogenation solution.

14. A process as claimed in claim 13, wherein the monocarboxylic acid is selected from the group consisting of formic acid, acetic acid, propionic acid and benzoic acid.

15. A process as claimed in claim 13, wherein the amount of the monocarboxylic acid is in the range of 1 to 0.001 M in the sugar solution to be hydrogenated.

16. A process as claimed in claim 13, wherein the amount of the monocarboxylic acid is in the range of 0.2 to 0.001 M in the sugar solution to be hydrogenated.

17. A process as claimed in claim 1, wherein said hydrogenation conditions achieve a content of aldonic acid of less than 2% by dry substance content of the hydrogenation solution.

18. A process as claimed in claim 17, wherein the amount of the aldonic acid on the surface of the hydrogenation catalyst is less than 2% by wet weight of the hydrogenation catalyst.

19. A process as claimed in claim 18, wherein the amount of the aldonic acid is less than 1%.

20. A process as claimed in claim 18, wherein the amount of the aldonic acid is less than 0.5%.

21. A process as claimed in claim 1, wherein the process further comprises washing the catalyst with an alkali to regain the activity of the catalyst.

22. A process as claimed in claim 21, wherein the alkali is selected from NaOH and KOH.

23. A process as claimed in claim 1, wherein the catalyst is a metal catalyst, wherein the metal is selected from iron, copper, cobalt, nickel, ruthenium, rhodium, palladium, osmium, iridium and platinum.

24. A process as claimed in claim 23, wherein the catalyst is a sponge metal catalyst.

25. A process as claimed in claim 23, wherein the metal is nickel.

26. A process as claimed in claim 25, wherein the catalyst is selected from the group consisting of sponge nickel and supported nickel.

27. A process as claimed in claim 23, wherein the catalyst load is in the range of 1 to 30% of the initial sugar amount.

28. A process as claimed in claim 24, wherein the catalyst load is in the range of 2 to 20% by weight.

29. A process as claimed in claim 1, wherein the hydrogenation is performed in a hydrogenation reactor, which comprises a heat exchanger in a loop with the hydrogenation reactor.

30. A process as claimed in claim 1, wherein the hydrogenation process is performed as a batch process.

31. A process as claimed in claim 1, wherein the hydrogenation process is performed as a continuous process.

32. A process as claimed in claim 1, wherein the process provides a conversion of the sugar to the sugar alcohol of more than 99%.

33. A process as claimed in claim 32, wherein the process provides a conversion of the sugar to the sugar alcohol of up to 100%.

34. A process as claimed in claim 1, wherein the process provides a selectivity of the product sugar alcohol of more than 95%.

35. A process as claimed in claim 34, wherein the process provides a selectivity of the product sugar alcohol of more than 98%.

36. A process as claimed in claim 35, wherein the process provides a selectivity of the product sugar alcohol of more than 99%.

37. A process for catalytic hydrogenation of lactose to lactitol, comprising subjecting lactose to hydrogenation conditions that maintain catalyst activity during consecutive hydrogenations by limiting the content of lactobionic acid on the catalyst to less than 3% by wet weight of the catalyst,
wherein the hydrogenation conditions comprise:
introducing a lactose solution into a hydrogenation reactor at an initial temperature of 50 to 100° C.,
hydrogenating the lactose solution by gradual heating of the solution at a heating rate in the range of 0.2 to 1.5° C./min to a final hydrogenation temperature in the range of 100 to 140° C., wherein the difference between the initial hydrogenation temperature and the final hydrogenation temperature is in the range of 80 to 20° C., and
continuing the hydrogenation at the final hydrogenation temperature until a conversion of lactose to lactitol of more than 95% is achieved, whereby the content of lactobionic acid on the catalyst is limited to less than 3% by wet weight of the catalyst.

* * * * *